(12) United States Patent
Pocklington et al.

(10) Patent No.: US 9,779,210 B2
(45) Date of Patent: *Oct. 3, 2017

(54) ENTERPRISE MANAGEMENT SYSTEM

(71) Applicant: McKesson Technologies LLC, Alpharetta, GA (US)

(72) Inventors: William Lee Pocklington, Lansdale, PA (US); Edmund B. Moore, Jr., Ambler, PA (US); Scott Edward Fraser, Collegeville, PA (US); Beth Anne Kuzmak, Chester Springs, PA (US); Michael Sean Flanagan, Newton Square, PA (US)

(73) Assignee: McKesson Technologies LLC, Alpharetta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/994,823

(22) Filed: Jan. 13, 2016

(65) Prior Publication Data
US 2016/0125148 A1 May 5, 2016

Related U.S. Application Data

(63) Continuation of application No. 11/430,753, filed on May 9, 2006, now Pat. No. 9,269,117.

(60) Provisional application No. 60/679,686, filed on May 10, 2005.

(51) Int. Cl.
G06Q 50/22 (2012.01)
G06F 19/00 (2011.01)
G06Q 10/10 (2012.01)

(52) U.S. Cl.
CPC ........ G06F 19/327 (2013.01); G06F 19/3418 (2013.01); G06Q 10/10 (2013.01); G06Q 50/22 (2013.01)

(58) Field of Classification Search
CPC ... G06F 19/327; G06F 19/3418; G06Q 10/10; G06Q 50/22
See application file for complete search history.

(56) References Cited

U.S. PATENT DOCUMENTS

| | | | |
|---|---|---|---|
| 5,119,455 A | 6/1992 | Jennings et al. | |
| 5,225,976 A | 7/1993 | Tawil | |
| 5,301,105 A | 4/1994 | Cummings, Jr. | |
| 5,455,948 A | 10/1995 | Poole et al. | |
| 5,519,607 A | 5/1996 | Tawil | |
| 5,524,253 A | 6/1996 | Pham et al. | |
| 5,774,660 A | 6/1998 | Brendel et al. | |

(Continued)

OTHER PUBLICATIONS

Bajec et al.,"A methodology and tool support for managing business rules in organisations",Jul. 2004,Science Direct,Volumn 30, pp. 423-443.*

(Continued)

Primary Examiner — Alexander Khong
(74) Attorney, Agent, or Firm — Alston & Bird LLP

(57) ABSTRACT

A health care enterprise management system and method of management are disclosed. The system and method include a routing layer, a plurality of applications in an application layer, wherein the application layer communicates external to the enterprise manager via communicative contact through the routing layer, a business rules layer of a plurality of health care provision business rules, and a core layer.

20 Claims, 38 Drawing Sheets

(56) References Cited

U.S. PATENT DOCUMENTS

| | | |
|---|---|---|
| 5,915,241 A | 6/1999 | Giannini |
| 5,924,074 A | 7/1999 | Evans |
| 5,960,200 A * | 9/1999 | Eager .................. G06F 8/30 703/13 |
| 6,004,276 A | 12/1999 | Wright et al. |
| 6,108,711 A | 8/2000 | Beck et al. |
| 6,393,404 B2 | 5/2002 | Waters et al. |
| 6,704,873 B1 | 3/2004 | Underwood |
| 6,826,536 B1 | 11/2004 | Forman |
| 6,847,981 B2 | 1/2005 | Song et al. |
| 6,978,247 B1 | 12/2005 | Bogart et al. |
| 7,017,142 B1 | 3/2006 | Ehnebuske et al. |
| 7,111,780 B2 | 9/2006 | Broussard et al. |
| 7,143,051 B1 | 11/2006 | Hanby et al. |
| 7,203,654 B2 | 4/2007 | Menendez |
| 7,328,233 B2 | 2/2008 | Salim et al. |
| 7,529,682 B2 | 5/2009 | Geller |
| 7,769,996 B2 | 8/2010 | Randle et al. |
| 7,849,498 B2 | 12/2010 | Royer et al. |
| 8,457,980 B1 | 6/2013 | DeTore |
| 2002/0128877 A1 | 9/2002 | Levit |
| 2002/0184050 A1 | 12/2002 | Papageorge |
| 2003/0050804 A1 | 3/2003 | Hendershot |
| 2003/0069760 A1 | 4/2003 | Gelber |
| 2003/0216928 A1 | 11/2003 | Shour |
| 2003/0216938 A1 * | 11/2003 | Shour .................. G06F 19/324 705/2 |
| 2003/0216944 A1 | 11/2003 | Stavis |
| 2003/0216964 A1 | 11/2003 | Maclean |
| 2004/0064343 A1 | 4/2004 | Korpman et al. |
| 2004/0078228 A1 * | 4/2004 | Fitzgerald .............. G06F 19/322 705/2 |
| 2004/0078247 A1 | 4/2004 | Rowe |
| 2004/0117617 A1 | 6/2004 | Geller |
| 2005/0033612 A1 | 2/2005 | Donovan |
| 2005/0187948 A1 | 8/2005 | Monitzer et al. |
| 2005/0261944 A1 | 11/2005 | Rosenberger |
| 2006/0080139 A1 | 4/2006 | Mainzer |
| 2006/0106653 A1 | 5/2006 | Lis |
| 2006/0155756 A1 | 7/2006 | Stanev et al. |
| 2006/0178915 A1 | 8/2006 | Chao |
| 2006/0212378 A1 | 9/2006 | Hoffman |
| 2006/0265251 A1 | 11/2006 | Patterson |
| 2006/0265255 A1 | 11/2006 | Williams |
| 2007/0011032 A1 | 1/2007 | Bregante |
| 2007/0043595 A1 | 2/2007 | Pederson |
| 2007/0078682 A1 | 4/2007 | Zubak |
| 2007/0118399 A1 | 5/2007 | Avinash et al. |
| 2007/0143148 A1 | 6/2007 | Kol |
| 2007/0162308 A1 | 7/2007 | Peters |
| 2007/0203757 A1 | 8/2007 | Dibiasi |
| 2007/0219824 A1 | 9/2007 | Rawlings |
| 2007/0250352 A1 | 10/2007 | Tawil |
| 2007/0288253 A1 | 12/2007 | Cobb et al. |

OTHER PUBLICATIONS

ScienceDirect,"A methodology and tool support for managing business rules in organisations",Version Dates Info,pp. 1.*

Extended European Search Report dated Jun. 23, 2010 corresponding to European Patent Application No. 06770135.9.

International Search Report dated Apr. 30, 2008 from corresponding International Application No. PCT/US2006/017912.

Statement in accordance with the Notice from the European Patent Office dated Oct. 1, 2007 concerning business methods (OJ EPO Nov. 2007, 592-593); XP002456252.

Written Opinion from International Patent Application No. PCT/US06/17912 dated Apr. 30, 2008, 5 pages.

International Preliminary Report on Patentability from International Patent Application No. PCT/US06/17912 dated Jun. 24, 2008, 5 pages.

Office Action from Canadian Patent Application No. 2,608,265 dated Jun. 3, 2013, 3 pages.

Office Action from Canadian Patent Application No. 2,608,265 dated Jun. 11, 2014, 5 pages.

Office Action from Canadian Patent Application No. 2,608,265 dated Jun. 23, 2015, 7 pages.

Notice of Allowance from U.S. Appl. No. 11/430,753 dated Jan. 22, 2016, 2 pages.

Notice of Allowance from U.S. Appl. No. 11/430,753 dated Dec. 30, 2015, 2 pages.

Notice of Allowance from U.S. Appl. No. 11/430,753 dated Oct. 13, 2015, 17 pages.

Office Action from U.S. Appl. No. 11/430,753 dated Dec. 11, 2014, 13 pages.

Examiner's Answer to Appeal Brief from U.S. Appl. No. 11/430,753 dated Oct. 26, 2011, 16 pages.

Office Action from U.S. Appl. No. 11/430,753 dated Feb. 10, 2011, 17 pages.

Office Action from U.S. Appl. No. 11/430,753 dated Mar. 11, 2010, 20 pages.

Office Action from U.S. Appl. No. 11/430,753 dated Jun. 25, 2009, 16 pages.

Office Action from U.S. Appl. No. 11/430,753 dated Dec. 11, 2008, 20 pages.

Office Action from U.S. Appl. No. 11/430,753 dated Feb. 19, 2008, 15 pages.

Patent Board Decision from U.S. Appl. No. 11/430,753 dated Sep. 30, 2014.

Pre-Appeal Conference Decision from U.S. Appl. No. 11/430,753 dated Jul. 22, 2011.

* cited by examiner

|   | _ | □ | X |
|---|---|---|---|

Edit  Navigate  File  | Mode |  Reports  Tools  Help

Providers | Practitioner Alt+1 | Locations | Provider Liability | Contracts | Integrator
Provider    Alt+2

[+] sunt

——Provider Data——
Tax ID
Provider Name         ABC

Displayed Provider Name
ABC                   ABC

——Attributes——

——Provider Billing Address——
Foreign Address

——Phone number——

[New] [Save] [Delete]

Provider Attributes
[New] [Save]

Name: G Rossi and R Grossi MD PC
Provider ID:01-2662398
Address:
Specialty: Thoracic Surgery
Status: Par

| Edit Navigate File Mode | Reports Tools | Help | | |
|---|---|---|---|---|
| Practitioner | Credentialing | Hospitals | Assessments | Contacts | Integrator | officias

Insurance Policies

Insurance Carriers

Policy Number

Expiration Date

Coverage

Name: G Rossi and R Grossi MD PC
Provider ID:01-2662398
Address:
Specialty: Thoracic Surgery
Status: Par

Figure 12

| Edit Navigate File Mode Reports Tools Help | | | | |
|---|---|---|---|---|
| Practitioner | Credentialing | Hospitals | Assessments | Contacts | Integrator |

⊞ Duis

Credentialing Cycles
⊞
⊞
☐ Show Current Cycle
Credentialing Type

Status

Committee Date

Start Date    End Date

Credentialer

Affiliated Agency

Specialty Verification | Hospital Verification

[Save] [Delete] [Undo]

Date:

By:

Source:

Notes:

Name: G Rossi and R Grossi MD PC
Provider ID:01-2662398
Address:
Specialty: Thoracic Surgery
Status: Par

| Main Menu |
|---|
| Reporter Menu |
| Report Template Configuration |
| Purge Expired Reports |

Figure 31

| Folders | | |
|---|---|---|
| [+] | Administration Reports | |
| [+] | Contracting Reports | |
| [+] | Credentialing Reports | |
| [+] | Maintenance Reports | |
| [+] | Management Reports | |
| [+] | Provider Relations Reports | |

| Templates |
|---|

| Reports | | | | View All Reports |
|---|---|---|---|---|
| Reports | Owner | Date Created | Date Expires | Action |

Figure 32

| Folders |
|---|
| [+] Administration Reports |
| [+] Contracting Reports |
| [+] Credentialing Reports |
| [+] Maintenance Reports |
| [+] Management Reports |
| [+] Provider Relations Reports |
| [+] Site Visit Reports |
| [+] System Reports |

| Templates |
|---|
| Re- Credentialing List |
| ABC |

| Reports | | | | View All Reports |
|---|---|---|---|---|
| Reports | Owner | Date Created | Date Expires | Action |
| [+] Re- Credentialing List | | | | [+] [+] [+] |
| [+] Re- Credentialing List | | | | [+] [+] [+] |
| [+] Re- Credentialing List | | | | [+] [+] [+] |

Enterprise search

Search Logic Controls                                  In Network [Utbv]

Practitioner Search

First Name: [          ]          Last Name [          ]

Gender Preference              Specialty [          ]
Male ○   Female ○              Hospital Privileges [          ]

[☐]    Provider Search

[Provider Name]                       [Provider Type]

Geographical Search

[City]          [State]                [Country]

[☐]    ID Search
[Perform on ID Search]

[Search]

Figure 37

ENTERPRISE MANAGEMENT SYSTEM

CROSS REFERENCE TO RELATED APPLICATIONS

This application is a continuation of U.S. patent application Ser. No. 11/430,753 entitled "Enterprise Management System," filed on May 9, 2006, which claims the benefit of U.S. Provisional Application No. 60/679,686 that was filed May 10, 2005, the entire contents of which are incorporated by reference herein.

BACKGROUND OF THE INVENTION

1. Field of the Invention

The invention relates to information flow, and, more specifically, to a system and method for enterprise information and transaction management.

2. Description of the Background

A successful business enterprise necessitates that effective interactions occur between the business employees, principals, management, peers, subordinates, supporting departments, suppliers, customers, clients, and authorities, and the information that each party in a business transaction requires to do his or her part in generating a successful enterprise transaction. Such enterprise level interactions may employ multiple parties at different levels of the transaction.

To facilitate such complex enterprise interactions occurring at multiple hierarchical levels substantially simultaneously, parties at each level of the interaction may require information about other parties at other hierarchical levels, in order to successfully fulfill the transaction. Further, planning and execution of transactions, and the associated logistics, which may occur at multiple locations, may further complicate the application of structure and organization to business transactions. As such, considering the parties and logistics, and the information flow, needed to carry out such hierarchical enterprise transactions, such transactions often become very disorganized, costly, and, worse yet in the health care field, may not be able to occur at all.

Consequently, the need to apply rules to transactions, and to information flow that enables transactions, in a hierarchical enterprise transaction system, exists, but, as yet, has not allowed for smooth transactions and information flow in complex enterprise hierarchies, such as in the health care industry.

Thus, there is a need to provide an integrated enterprise solution for the application of rules and structure to hierarchical transactions, and to the information flow that is necessarily associated with hierarchical transactions.

SUMMARY OF THE INVENTION

The present disclosure includes a health care provision enterprise manager, management system, and method of management. The manager, system, and method include a routing layer, a plurality of applications in an application layer, wherein the application layer communicates external to the enterprise manager via communicative contact through the routing layer, a business rules layer of a plurality of health care provision business rules, and a core layer.

The core layer may be substantially simultaneously accessible to each of the health care provision business rules, and at least one subset of the health care provision business rules may be correspondent to each of the applications in the application layer. At least one business rule in each of at least two subsets may be substantially simultaneously accessible to at least two of the applications.

Thus, the present disclosure provides an integrated enterprise solution for the application of rules and structure to hierarchical transactions, and to the information flow that is necessarily associated with hierarchical transactions.

BRIEF DESCRIPTION OF THE FIGURES

FIGS. 2 through 39 are screens or pages illustrating of various aspects of the system of FIG. 1.

DETAILED DESCRIPTION OF THE PREFERRED EMBODIMENTS

Figure 1:
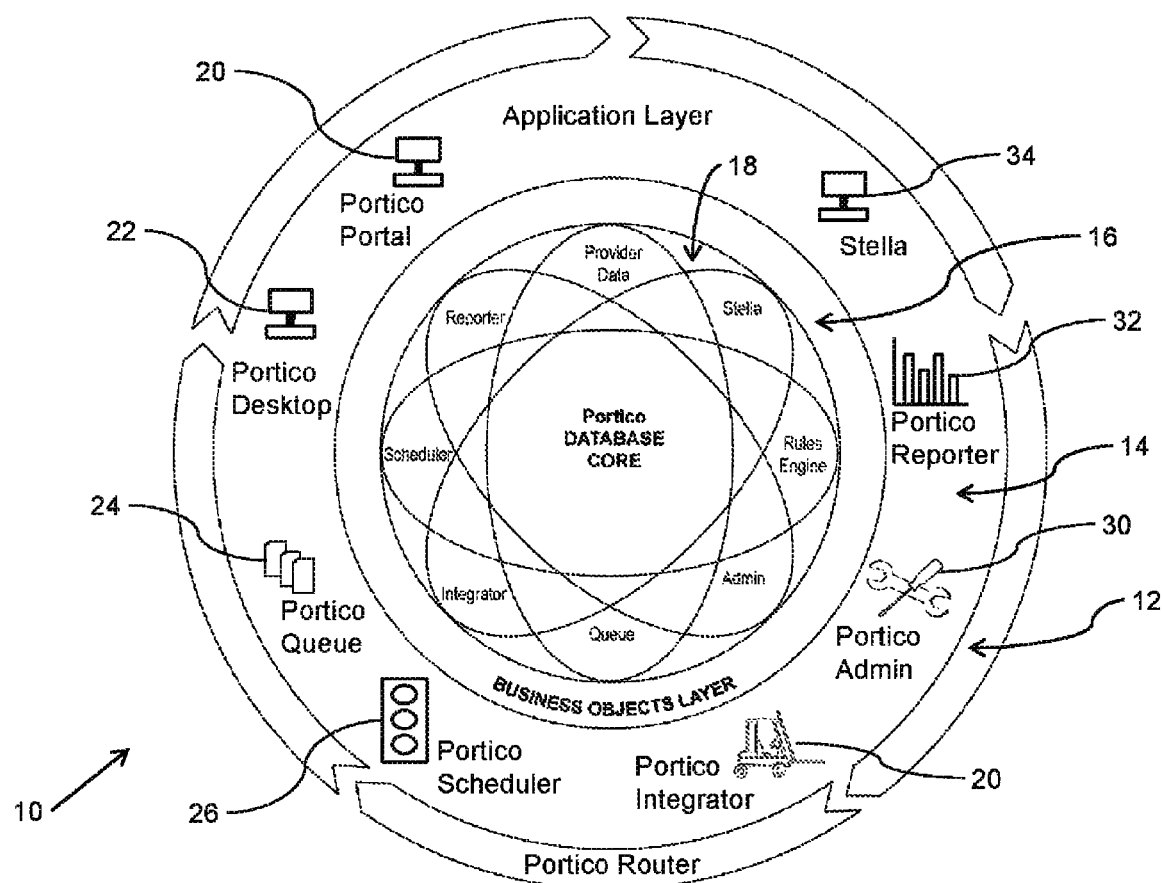
FIG. 1 is a diagrammatic representation of an exemplary embodiment of a hierarchical enterprise information management system according to the present disclosure.

Referring now to the figures and in particular to FIG. 1, an enterprise management system 10 according to the present disclosure is shown.

Information management in a variety of business settings necessitate that information be managed for an entire business enterprise. Advantageously, the system 10 hierarchically manages all aspects and provisions of such an enterprise.

For purposes of clarity, system 10 is described herein below in use in the health care industry, and more particularly in use by a health care provider plan (hereinafter referred to as the "plan" or "HCPP"). Of course, it is contemplated by the present disclosure for the system 10 to find use with any enterprise that requires the ability to perform multiple hierarchical transactions.

In the health care industry, a "health care provider" or "provider" is generally referred to as the person or entity that provides health care services to a patient. For example, a provider can include an individual doctor, a group of doctors, a hospital, a group of hospitals, a therapist, and the like.

Typically, health care providers honor, or are participate with, certain insurance types or plans (hereinafter referred to as a "plan"). Consequently, the provider provides health care to patients that are members of that plan and is compensated for such services under the terms of a contract with the plan.

Before the plan accepts a particular provider as participating with the plan, the plan first typically reviews the credentials of that provider. The task of credentialing a provider may necessitate applications and business rules that verify credentials stored in a database, and that track a yes or no acceptance of the provider through those applications and rules.

The plan and the provider then agree to certain contract terms regarding the services, costs, and the like. For example, the task of contracting the provider by the plan may assign a level to the provider such as a "normal provider" or a "preferred provider". Further, contracting the provider by the plan may include tiering for different service types or locations of that provider. In some instances, a provider may be paid by the plan in accordance with the number of members or patients of that provider's panel, rather than the number of members seen per day, week, or month, for example, as will be apparent to those skilled in the art.

As illustrated in FIG. 1, the enterprise management system 10 includes a plurality of layers, wherein each layer provides one or more functions of the system. The layers may include, for example, a routing layer 12, an application layer 14, a business rules or objectives layer 16, and a core layer 18. The enterprise management system 10 can be made available to any of the users of the plan, such as, but not limited to, the employees of the plan, the health care provider, the members, and others.

The routing layer 12 may, for example, provide connectivity between the system 10 and external applications or devices (not shown). Thus, system 10 may, via the routing layer 12, be accessible remotely, in whole or in part. For example, aspects of the system 10 may be provided separately at a plurality of locations, and each such aspect may be in communication with other aspects performing one or more functions via the routing layer 12. The routing layer 12 may perform, for example, routing for the layers (e.g., layers 14, 16, 18) below the routing layer, such as application layer information or communications. Routing layer 12 may include, for example, socket numbers, nodes, data points, or like information required for routing of the information from the layers below the routing layer.

The application layer 14 may provide, for example, applications accessible to one or more users to perform one or more functions. Such applications may be available, via the routing layer 12, at the same location as the user, or at a location remote from the user. Each application may provide a graphical user interface (GUI) for ease of interaction by the user with information resident in the layers (e.g., 16, 18) lower than the application layer 12. The GUI may be specific to a user, set of users, or type of user, or may be the same for all users or a selected subset of users. Applications in the application layer may include, for example, an Internet portal 20, a desktop 22, a queue 24, a scheduler 26, an integrator 28, an administrator 30, a reporter 32, and a remote application data collector 34.

The Internet portal 20 may be a portal that provides, via the GUI, remote access to and from the system 10. The Internet portal 20 may be, for example, a network browser. The Internet portal 20 may include the ability, either automatically based upon a user request in another application, or by a user request, to "hook", search, or otherwise retrieve particular data from one or more remote points, such as on the Internet. The Internet portal 20 may vary by user type, or may be available to only a certain user type, such as the healthcare provider.

The desktop 22 may be, for example, a master GUI set that allows a user to select or interact with GUIs of any of the applications in the application layer 14. For example, the desktop 22 may allow a user to simultaneously access a variety of information available through two or more of the applications in the application layer 14.

The queue 24 causes, responsively to one or more user instructions, one or more rules in the rules layer 16 to be applied to force the performance of tasks in a certain order. For example, the queue 24, based on a user request, may cause a first user (i.e., John Doe) to be asked to perform a given task only after a second user (i.e., Jane Doe) has completed a preceding task. There may also be multiple queues in which tasks and instructions regarding tasks and rules reside.

The scheduler 26 can schedule tasks according to triggers. For example, tasks may be scheduled for repetition at certain times or based on certain events, or may be scheduled to occur only once, at a given time or upon a triggering event. The time or event used to cause a scheduled event is herein referred to as a "trigger". The trigger for one or more events may be varied using the scheduler 26.

The integrator 28 may illustrate, report, and govern on the passing of information to and from the system 10. The integrator 28 may illustrate the application, point, or node, for example, to or from which information was passed. The integrator 28 may illustrate the meeting of a particular criteria to pass data, the reason the criteria was met, and whether data passed responsively to the meeting of the criteria. Data can be blocked from passage, or forced into passage, via the integrator 28. For example, the integrator 28 may govern and review the passing of data external to the system 10 in order to get an insurance claim check cut at the external point.

The administrator 30 may limit, for example, data manipulation, or information access. For example, the administrator 30 may allow for administration at one or more levels, such as an individual user level, at a client level, or at a system level. An administrative user may, via the administrator 30, enter access or use restrictions for other users below that user. For example, a client level administrative user may create or monitor access or use restrictions for users working at that client. Such restrictions may include, for example, the assignment of user names and passwords that allow the use of the system 10, or the selection of one or more data types that the subservient user is allowed to view or manipulate.

The reporter 32 may provide for the presentation of data that a particular user is eligible to see in one or more selectable formats. This data may be communicated to one or more external data application types. For example, the reporter 32 may layer reports, wherein additional information is available by viewing successively lower layers of a report. Such layers may be made available by the use of drop down menus, or tabbed folder files, for example. Reports may include autofill functionality, wherein data is filled responsively to the entry of partial data in a particular field by the user. In order to provide a plurality of report formats, such as spreadsheets or the like, and in order to provide communications with multiple external applications, the reporter 32 may provide reports in a generally readable format, such as XML. The reports may be user or plan defined according to attributes discussed further herein below. Default report templates and customized reports, such as scheduled reports or reports that invite people to log-in for review of the report, may thus be generated by the reporter 32.

The remote application data collector 34 may assist a user in the performance of remote data. For example, the remote data application collector may provide connectivity from a personal digital assistant (PDA), a bar code reader laptop computer, or the like, to the system 10. The remote application data collector 34 may communicatively connect to other applications in the application layer 14, such as via the routing layer 12. The remote application data collector 34 may allow for storage and manipulation of raw data as it is collected, such as at the point of collection, for subsequent, batch, or real time communication to the system of the present disclosure.

The business rules layer 16 may provide a communicative interface between the applications of the application layer 14 and business rules to be applied to the application in the application layer, and to the data and information from the core layer 18 as that data and information is manipulated by the applications of the application layer. The business rules layer 16 may include a defined set of allowable interactions between the applications in the applications layer 14 and the data in the core layer 18.

The business rules layer 16 may include a plurality of different sets of business rules, and each set of business rules may be corresponded to one or more applications in the application layer 14. The business rules layer 16 may, for example, include a rules engine (not shown). The rules engine may provide a plurality of selectable rules, or rule templates, wherein each rule in the rules engine has rule attributes that define the rule. Further, the rules engine may allow for modifications to the rules from one or more applications in the application layer 14, such as modification to rule triggers, for example. Advantageously, system 10 provides, via the rules engine of business rules layer 16, a definable variety of available rules that provide scalability to the system.

For example, the rules engine may provide rules having one or more rule layers. As each successive rule layer is satisfied, a subsequent rule layer may be applied. For example, each rule and rule layer may have a series of attributes. Satisfaction of certain attributes of a rule layer may trigger application of other attributes of that particular rule layer. Satisfaction of all attributes in a particular rule layer may trigger application of a subsequent or related rule layer. Rule attributes and layers maybe selectable from one or more of the GUIs in the application layer. Triggers for a rule may include the performance of certain tasks. In the present disclosure, tasks include processes or acts that are finite and definite.

The rules engine may interface, via the business rules layer 16, between the application in the application layer 14 and the core layer 18. The business rules layer 16 may have a dedicated database (not shown) for storage of the rules, or may make use of the database resident in the core layer 18. As such, a history of rules and rules changes may be kept in one or more databases, to thereby allow for rule tracking and rule reporting. Rules, once changed, may preferably be enforced on all data upon execution or upon synchronization of the new rule to the data. For example, changes in credentialing of a provider, the HIPPA regulations, changes in provider incentive programs, and the like, may regularly require rules changes that may need to be universally enforced, on an expedited basis, without the need to spend a lengthy time period engaging in review of all rules that might be affected by the change.

The database wherein the rules are maintained is preferably expandable, such as, for example, wherein a plurality of rules are initially available with regard to health care patients and health care providers, and wherein the database is expanded to include rules, such as health care claims rules that operate on the data and rules already present for patients and providers.

As such, rules for different layers or portions of a process may be added or modified from an application in the application layer 14, applied by a rules engine in the business rules layer 16, and enforced on data in the core layer 18. Thus, the data in the core layer 18 may allow for the credentialing of providers in a health care system through credentialing rules, contracting in a health care system through contracting rules, and application of claim rules to the same data in the core provided to the credentialing and contracting rules. Thereby, quality checks can be carried out at every stage in the health care process, thus improving quality control at each stage of the process, thus limiting the quality checks necessary at claim payment, and thus eliminating redundant manipulations of the same data from the core layer.

The core layer 18 may be accessed, for example, by the rules in the business rules layer 16. The core layer 18 may include, for example, one or more databases (not shown) containing a plurality of information. The plurality of information may include, for example, information relating to health care providers, patients, insurers, plans, institutions, entities, transactions, reports, and any other information associated with the field of health care. Such information may be combined in the one or more databases, or may be partitioned in the one or more databases.

Different user interfaces provided by the different applications in the application layer 14 may access the same rules in the business rules layer 16, and, thereby, the same, or portions of the same, information in the core layer 18. Advantageously, system 10 shares the same information between multiple rules and multiple applications, which increases efficiencies and provides redundant data checking.

Therefore, one or more libraries, languages, or the like, may be used, normalized, and/or stored in or between one or more databases in the core layer 18 or the business rules layer 16. Such libraries, languages, or the like, may include, for example, Java, C++, XML, HML, Object Class libraries, HL 7, or the like, as will be apparent to those skilled in the art. Thus, the system 10 preferably includes a normalization engine to allow for import and export from and to various data types, such as to allow for the importation of older data types into the system.

Data in the core layer 18 may be defined in accordance with a user instruction, such as an instruction entered via the applications in the application layer 14, the type of database used in the core layer, or as a system default. The definition of data in the core layer 18 may vary in accordance with the type of record, such as different data definitions for provider data, member data, advertiser data, marketer data, and insurance data. The data in the core layer 18 may have attributes defined in accordance with business rules in the business rules layer 16, and data may not be accepted until all attributes required by a given rule have been entered for a given data entry of a particular data entry type. Attributes may include, for example, names, locations, licensure numbers, copies of contracts, other credentials, insurance plans, and the like. Data attributes may be used to define relationships between different data entries in the core layer 18, and thus the data attributes create and enable connections between data entry for use by the rules for the applications, for example.

Certain data may be associated with the data in the core layer 18 by a link from the data entry in the core layer to an external data node of such as an entry point to the world-wide web or an Intranet, for example. Thus, either based on an association in the core layer, or by a rule in the business rules layer, or by a user request, such as a search, one or more data hooks may be sent external to the system of the present disclosure in order to obtain requested or otherwise associated information from an external entity.

Data in the core layer 18 may be manipulated from an application in the application layer 14 in accordance with permissions granted by rules in the business rules layer 16. Permissions may vary by data entry type. For example, a provider may change certain of that provider's attributes and certain of the attributes of the members associated with that provider, such as those members registered on that provider's panel. A member may change certain of that member's attributes, such as that member's home phone number, and likewise an insurer, an advertiser, a marketer, and the like may change particular information. The information that a certain party is eligible to change may be decided by an associated rule for that data entry type in the business rules layer 16, and may initially require a proper login. Certain attributes, such as the claim rules followed by a given insurer, may further be associated with the rules in the business rules layer 16.

FIGS. 2 through 39 are screen shots illustrating the system 10 of the present disclosure in use.

As seen in FIGS. 2-19, a user may select, access or interact with anyone of a variety of applications in the applications layer 14 via the desktop 22.

Such accessing of one application may occur by an accessing from within another application, due to the nature of each application accessing the same rules or core database information, as discussed herein above. The desktop 22 may be a "master access point" for other applications in the application layer 14. Further, each screen may provide, such as by a split screen methodology, a "quick glance" summary of information available under one or more tabs of a returned core database record.

Figure 2:
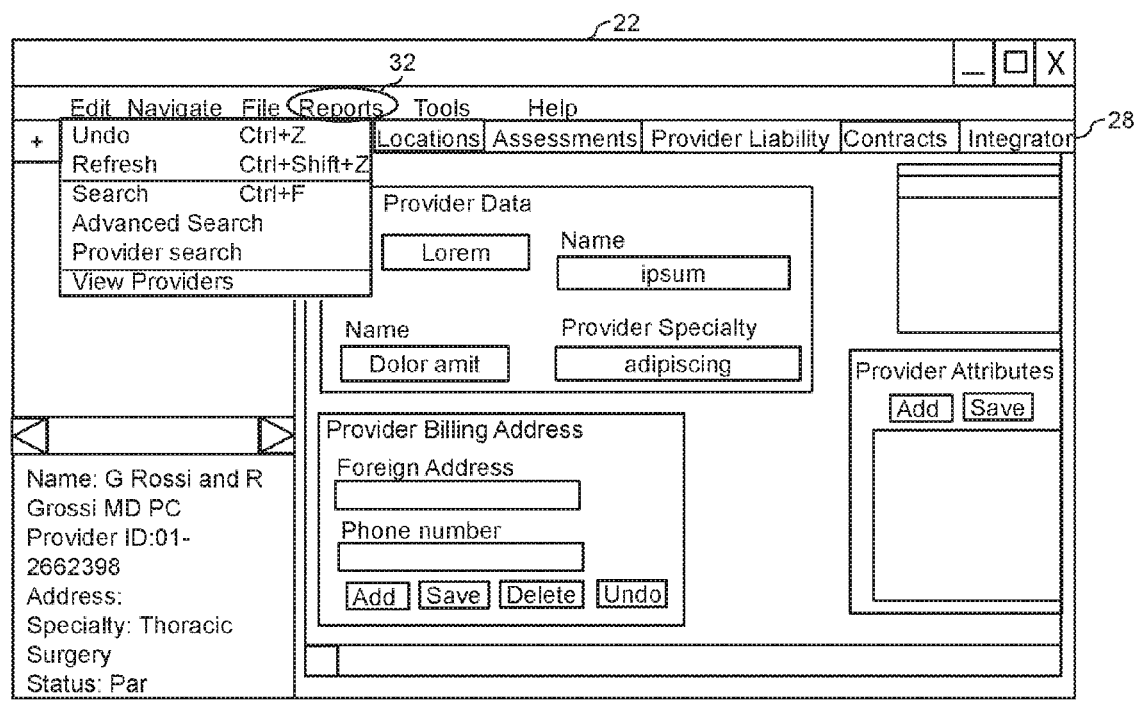
Figure 9:
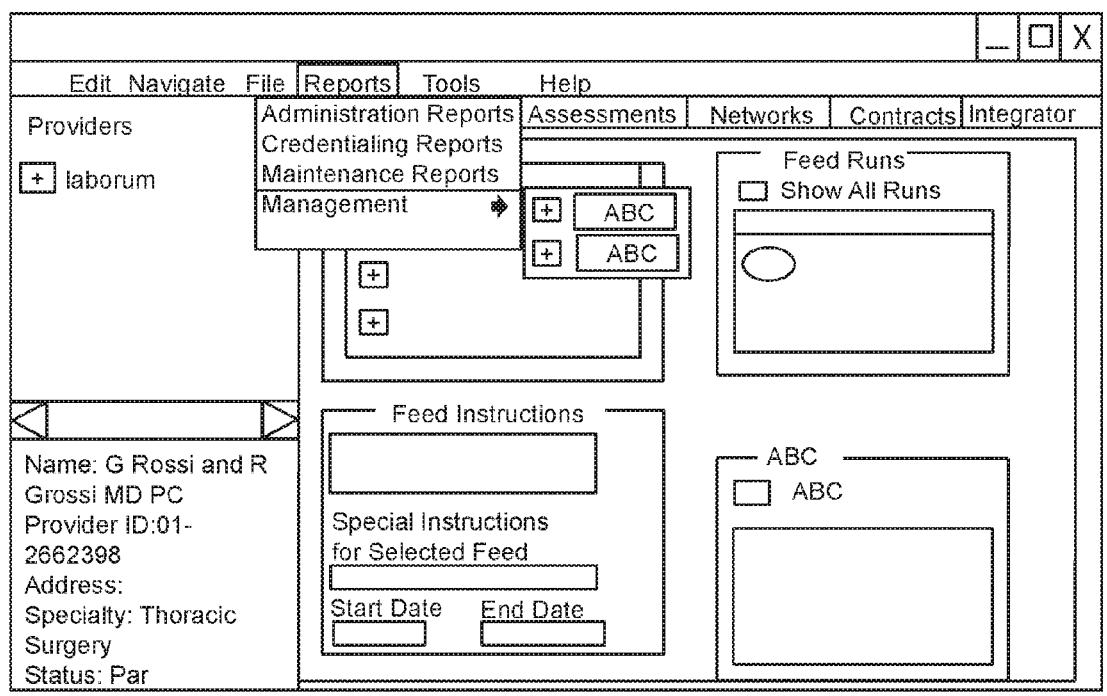
Figure 18:
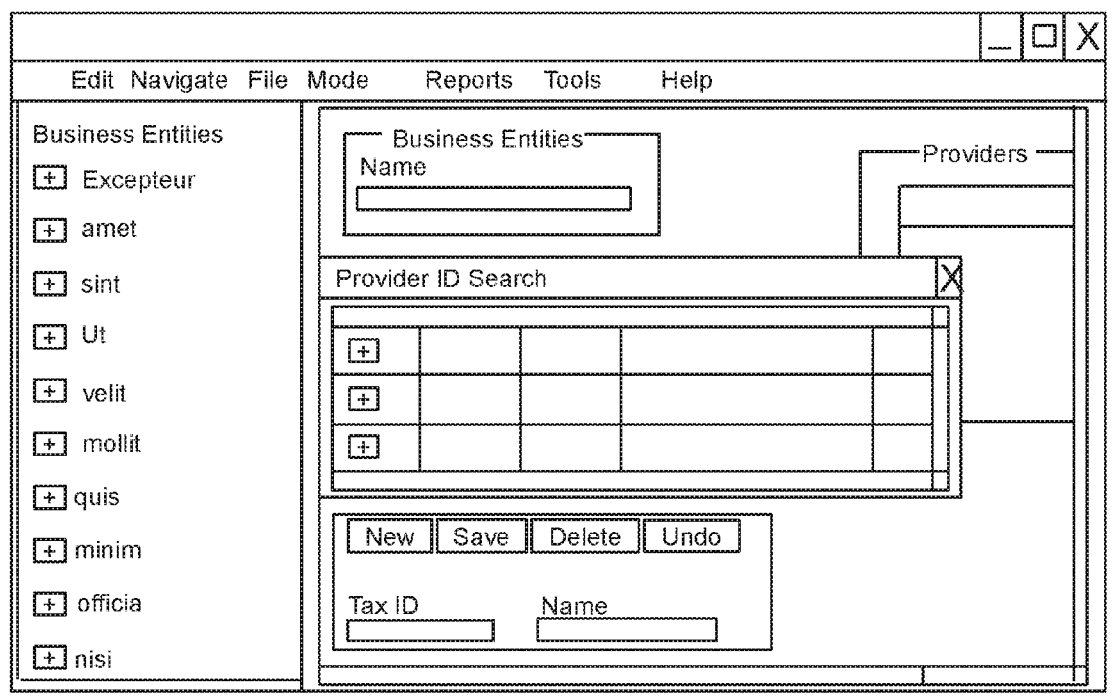
Figure 19:
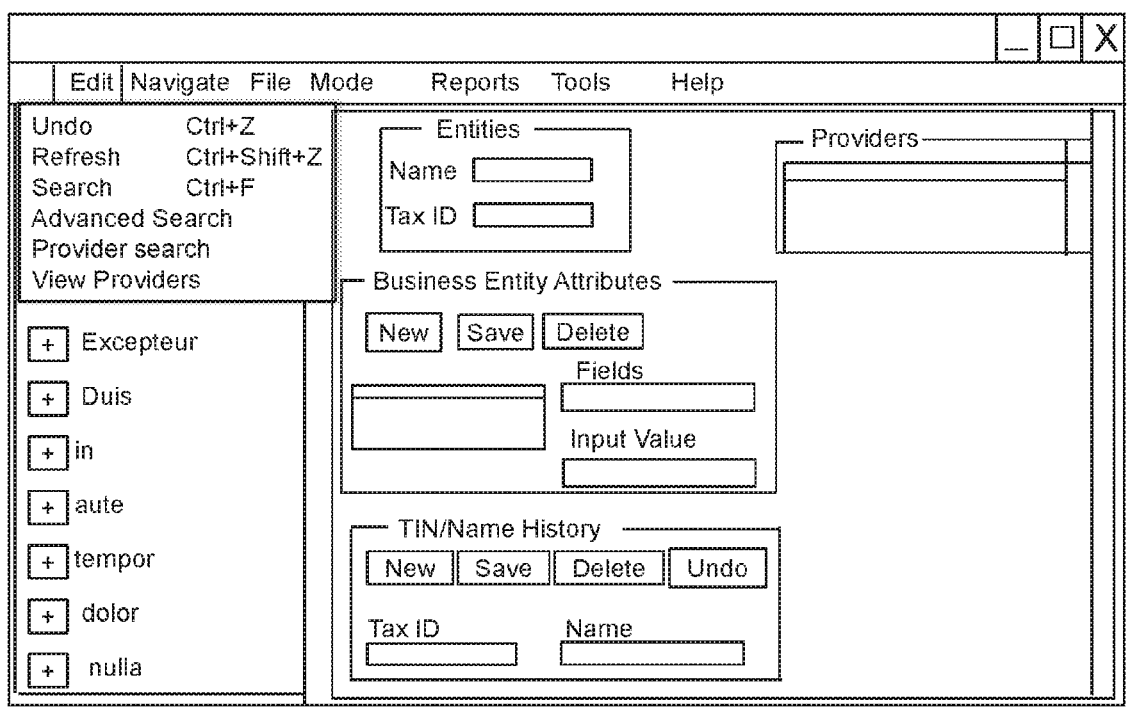

For example, as may be seen in FIG. 9, a user may select the reporter 32 via a Reports tab from the desktop 22 to view a variety of Reports, such as reports relating to Administration, Credentialing, Maintenance, Management, Provider Relations, Site Visit, or Systems, for example. As may be seen in FIG. 10, a user may select a Mode, such as Practitioner, Provider or Business Entity, for example, to access a set of associated applications there with. Also, as seen in FIG. 2, a user may edit any selection by selecting Edit from the desktop. Such editing may include refreshing the current screen, or performing a search such via entering a provider ID, name, or other identifiable information item into a search engine, or simply by viewing a list of practitioners, providers, or other listed entities from a database, the internet, or other information source accessible by the system, as seen in FIG. 18. Of note, a Provider ID, for example, may be an imported identifier from a legacy system that, once resident in the core database, may serve as a search term to find information. A search may, for example, autofill as a user types a search, or may allow for drill down into lower levels of information once a top-level hierarchical selection has been made.

Under the Practitioner Mode, a user may search for a practitioner and select any such practitioner identified to view information specific to that practitioner. For example, when a user selects Practitioner Mode, the user may further select an information category from a variety of categories, such as Credentialing, Specialties, Hospitals, Locations, Panels, Contracts, Integrator, Practitioner, Education, Additional Addresses, Insurance, Malpractice, and Networks, each of which categories may include tabbed, searchable information relevant to one or more practitioners. Each search result may be provided with tabs and hyperlinks, for example. Tabs may allow a user to vary between different information aspects related to the search result returned. Hyperlinks may allow for a drill down into lower-hierarchical layers for the search result obtained, or may allow a user to link to other information types from within a first information type.

For example, a practitioner result, under a "Provider" tab for that practitioner, may provide a hyperlink that, if selected by a user, refers the user to the Provider information screens correspondent to the hyperlinked Provider in the Practitioner screen.

Figure 11:
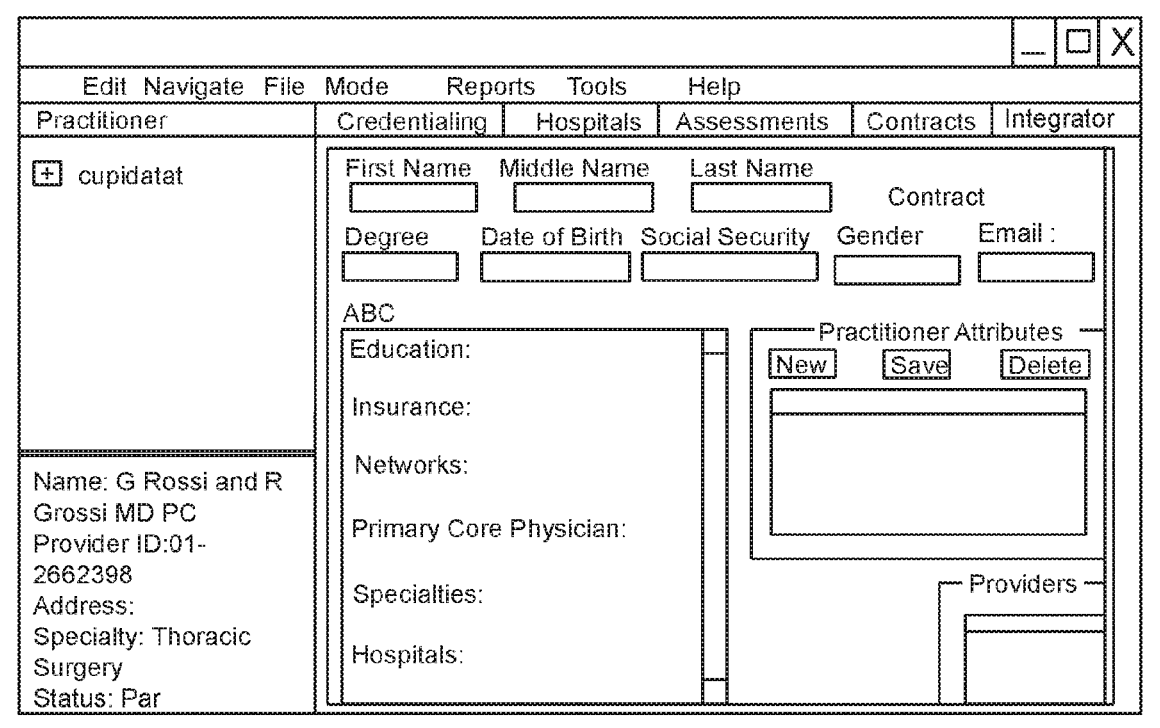

As may be seen in FIG. 11, a user may select Practitioner from the Practitioner Mode, and may view information regarding a specific practitioner. The information relating to the specific practitioner may be, for example, the first name, middle name, last name, suffix, salutation, degree, date of birth, social security number, gender, email, practitioner summary, which may further include information, such as education, insurance, networks, primary care physician, specialties, and hospitals. Practitioner information may also include a Provider ID, Provider Type, Address, Primary Specialty, Status, Practitioner Attributes, which may be newly Added, Deleted, or Saved, as well as providers associated with the specifically identified practitioner, for example.

As may be seen in FIG. 12, a user may select Insurance from the practitioner Mode, and may view information related to insurance associated with a particular practitioner. Such information may include any listed Insurance Policies, as well as information regarding Insurance Carriers, Policy Numbers, Expiration Dates, and Coverage, for example.

Figure 13:
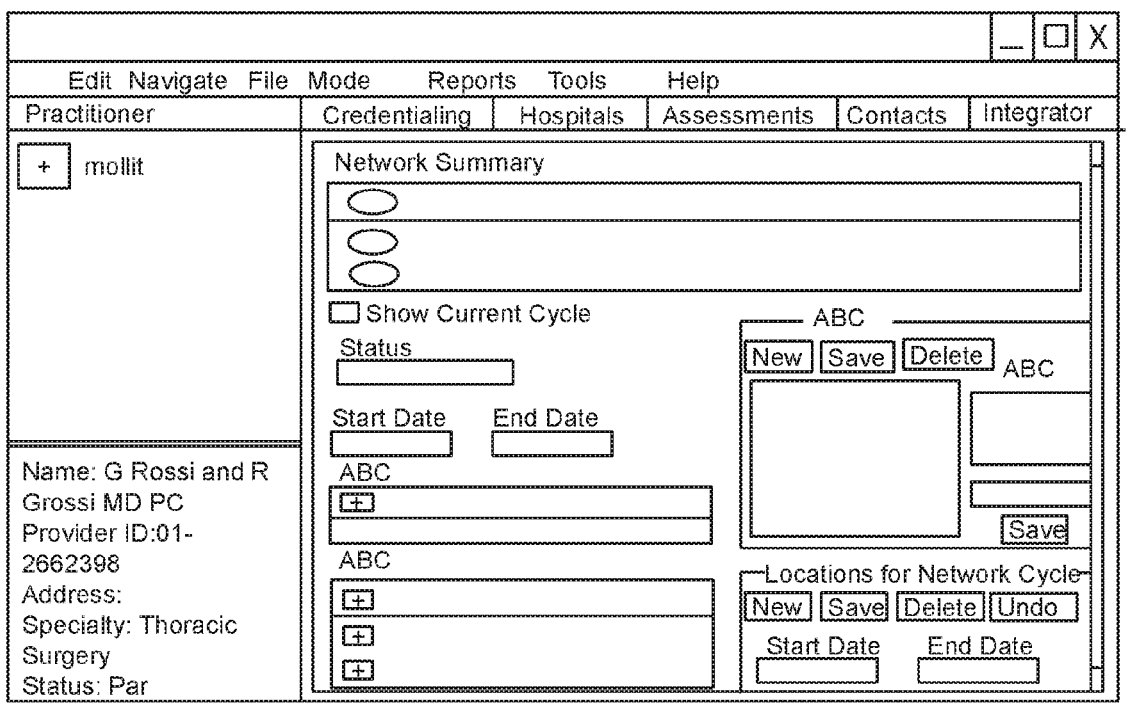

As may be seen in FIG. 13, a user may select Networks from the Practitioner Mode, and may view information related to any Network associated with a particular practitioner. Such information may include a Network Summary, Network, Network Effective Date, Status, Start Date, End Date, Specialties for Network Hospitals for Network Practitioner Network Cycle Attributes, which may be added to, deleted or saved, Locations for Network Cycle, which may also be added to, deleted or saved, and a Parent Network Cycle, with a Start Date and an End Date, for example.

As may be seen in FIG. 14, a user may select Credentialing from the Practitioner Mode, and may view information related to credentialing issues associated with a particular practitioner. Such information may include Credentialing Cycles, Credentialing Type, Status, Committee Date, Start Date, End Date, Credentialer, Affiliated Agency, Recruited By, and Specialty Verifications and Hospital Verifications, both of which may further include information regarding Date, By, Source, and Notes, for example. Further still, information regarding Specialty Verifications and Hospital Verifications may both be added to, deleted or saved.

Figure 15:
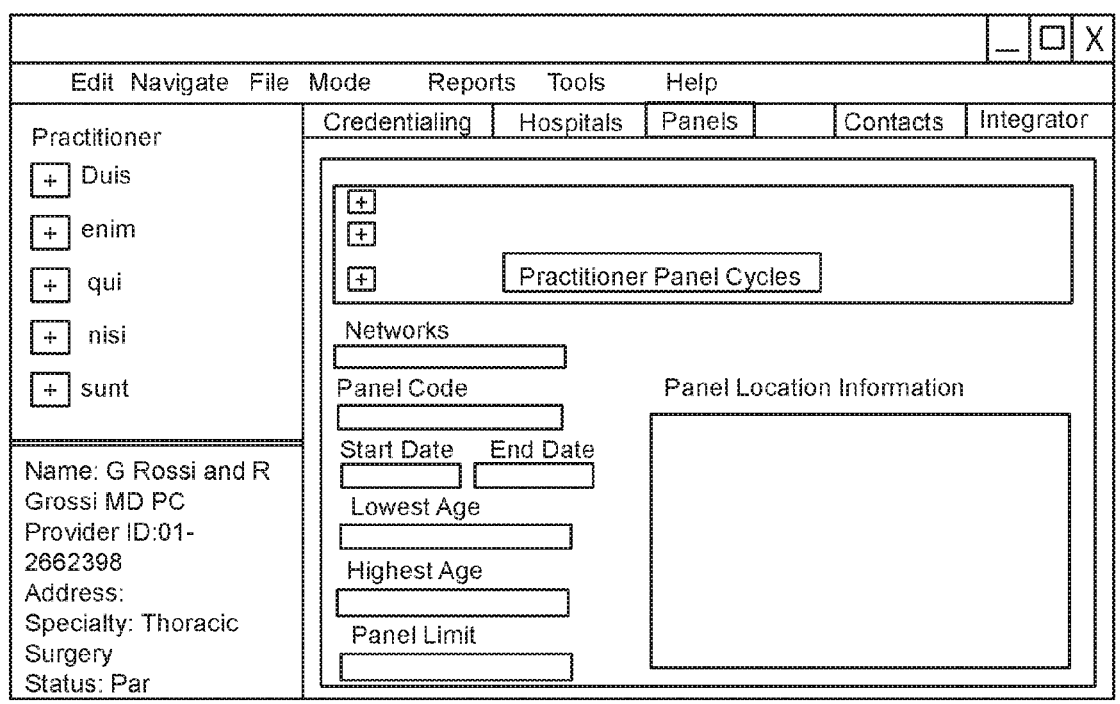

As may be seen in FIG. 15, a user may select Panels from the Practitioner Mode, and may view information related to panel issues associated with a particular practitioner. Such information may include Practitioner Panel Cycles, Network, Panel Code, Panel Status, Start Date, End Date, Lowest Age, Highest Age, Panel Limit, and Panel Location Information, for example.

Figure 16:
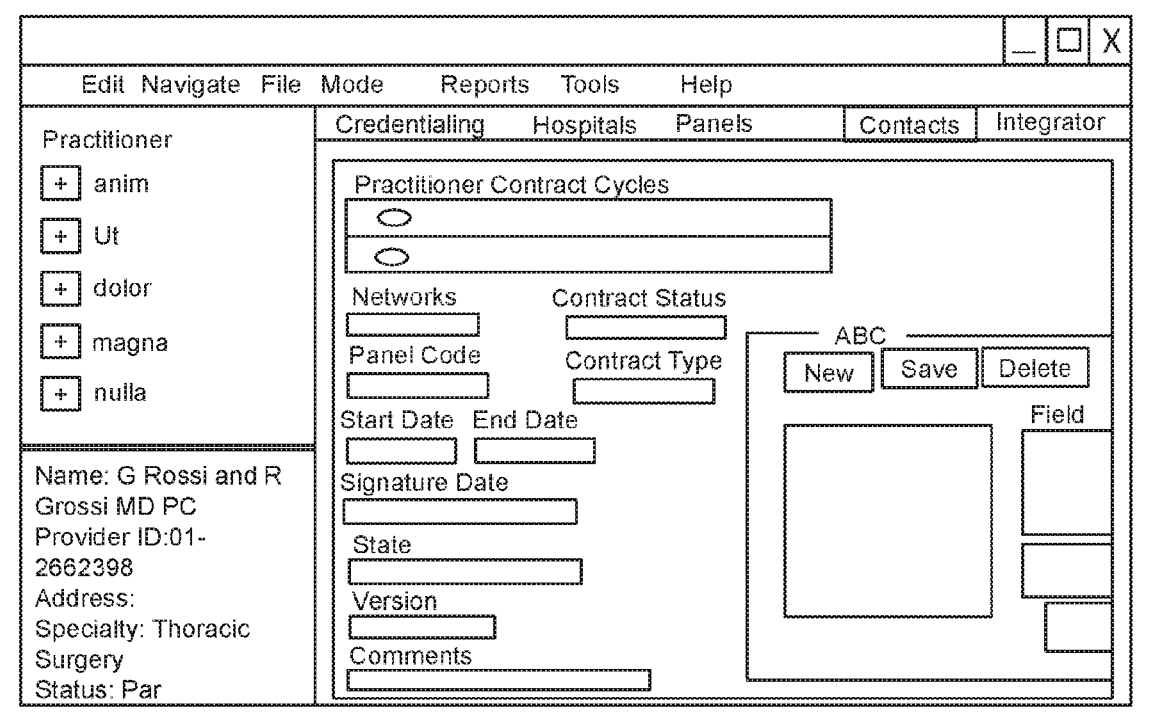

As may be seen in FIG. 16, a user may select Contracts from the Practitioner Mode, and may view information related to contract issues associated with a particular practitioner. Such information may include Practitioner Contract Cycles, Network, Start Date, End Date, Signature Date, Negotiator, State, Version, Contract Status, Contract Type, Fee Code, Rate Table, Contract Area, Termination Reason, and Comments, for example. Further information regarding Practitioner Contract Attributes, which may be added to, deleted or saved, may also be viewed and manipulated by the user.

Under the Provider Mode, a user may search a provider database for a provider and select any such provider identified to view information specific to that provider. For example, when a user selects Provider Mode, the user may further select an application from a variety of applications, such as Providers, Locations, Additional Addresses, Affiliations, Assessments, Networks, Provider Liability, Contracts, and Integrator.

As may be seen in FIG. 2, a user may select Providers from the Provider Mode, and may view information related to a particular provider. Such information may include tax ID, Provider Name, Provider Name Indicator, Displayed Provider Name, Provider Medicare Number, Provider Specialty, Provider Billing Address, Phone Numbers (which may be added to, deleted or saved), Provider Attributes (which may be added to, deleted or saved), and Practitioners within that Provider, for example.

Figure 3:
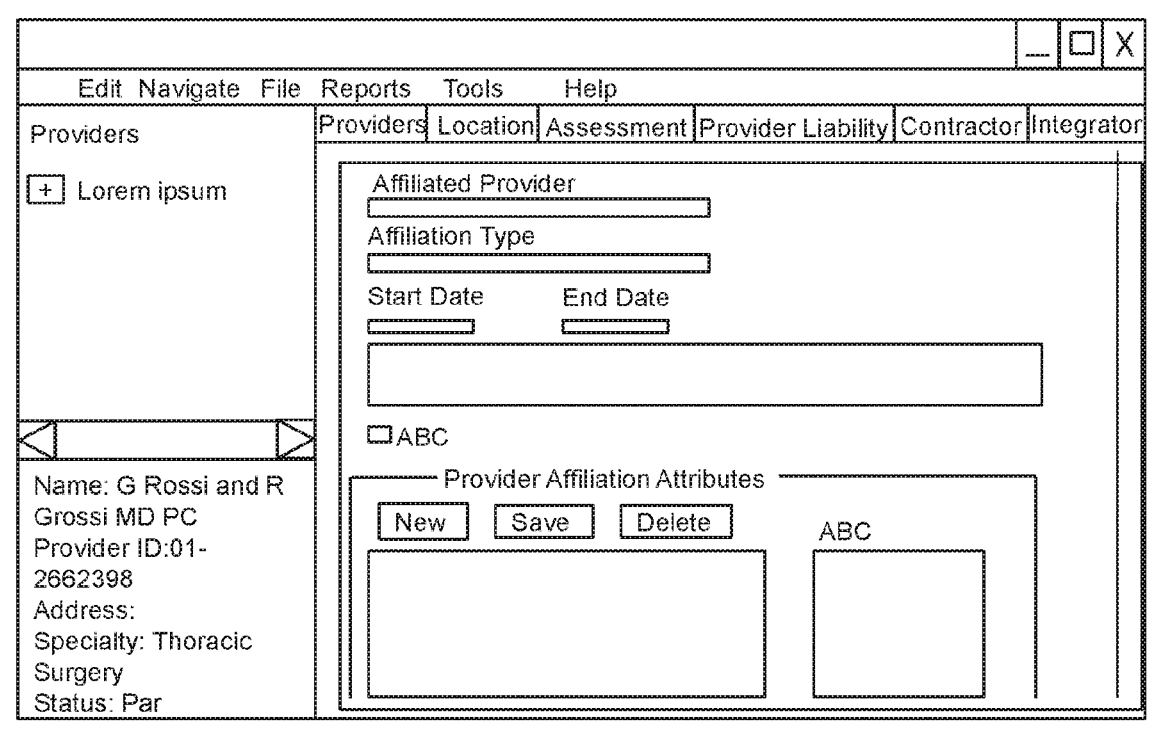

As may be seen in FIG. 3, a user may select Affiliations from the Provider Mode, and may view information related to affiliation issues associated with a particular provider. Such information may include Affiliated Provider, Affiliation Type, Start Date, End Date, and Provider Affiliation Attributes, which may be added to, deleted, or saved, for example.

Figure 4:
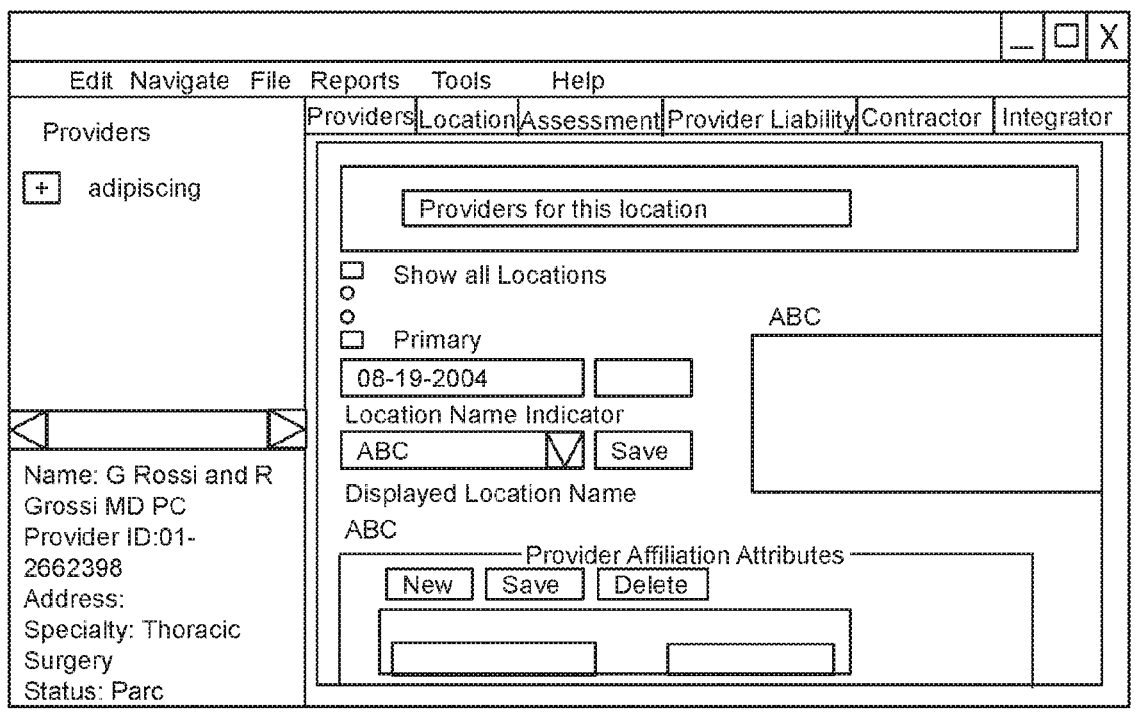

As may be seen in FIG. 4, a user may select Locations from the Provider Mode, and may view information related to location issues associated with a particular provider. Such information may include Locations (which may be ordered by Location Name or by Address), Start Date, End Date, Location Name Indicator, Displayed Location Name, Provider Location Attributes, which may be added to, deleted, or saved, and Practitioners, for example.

Figure 5:
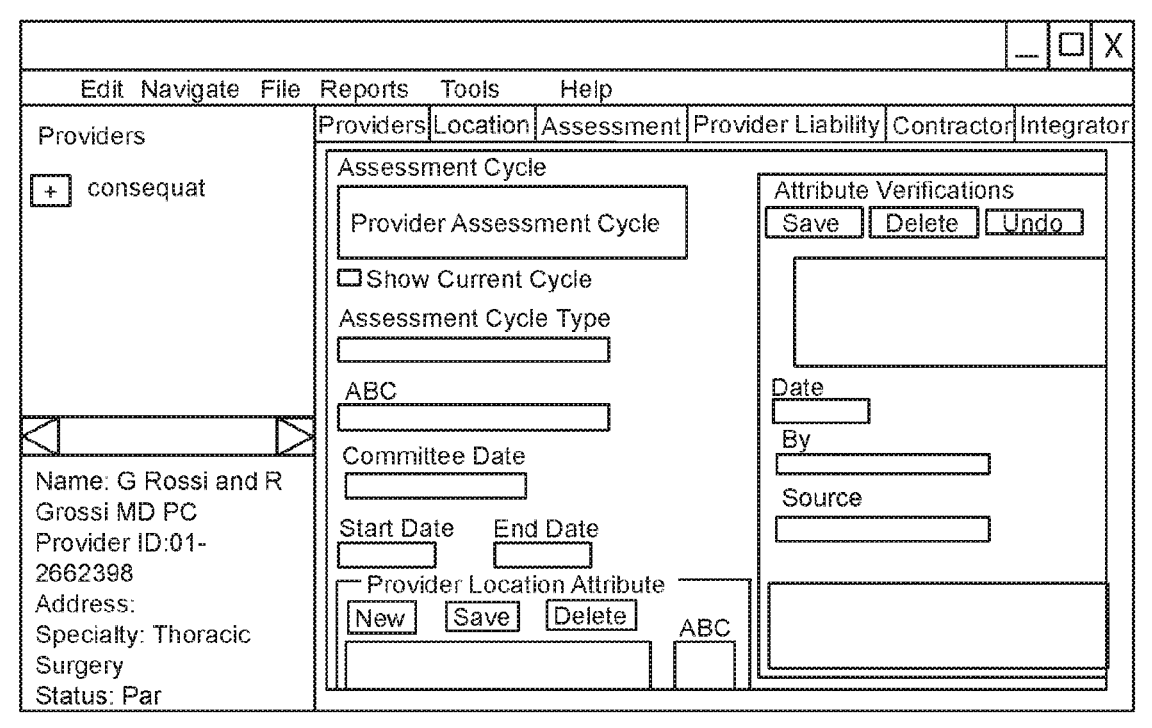

As may be seen in FIG. 5, a user may select Assessments from the Provider Mode, and may view information related to assessment issues associated with a particular provider. Such information may include Assessment Cycle, Assessment Cycle Type, Status, Committee Date, Start Date, End Date, Provider Assessment Cycle Attributes, which may be added to, deleted, or saved, and Attribute Verifications, which may also be added to, deleted, or saved, and contain further information regarding Date, By, Source, and Notes, for example.

Figure 6:
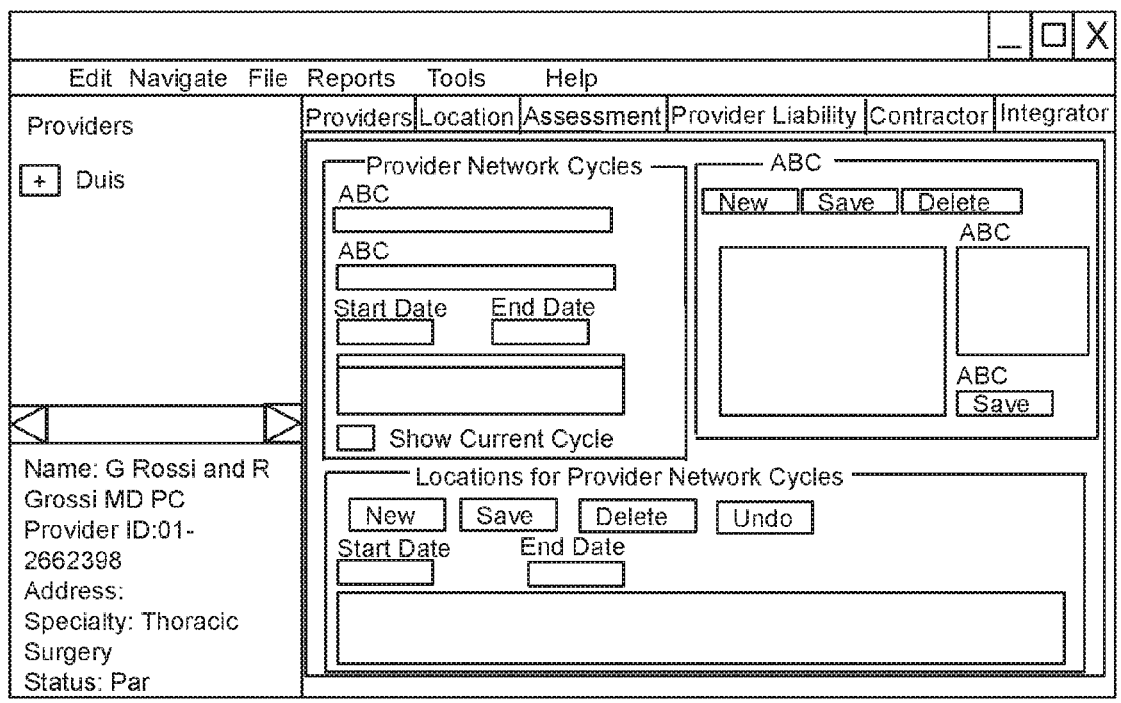

As may be seen in FIG. 6, a user may select Networks from the Provider Mode, and may view information related to network issues associated with a particular provider. Such information may include Provider Network Cycles, which may further include Network, Network Status, Start Date, and End Date, Provider Network Cycle Attributes, which may be added to, deleted, or saved, and Locations for Provider Network Cycles, which may also be added to, deleted, or saved, and further includes information regarding Start Date and End Date, for example.

Figure 7:
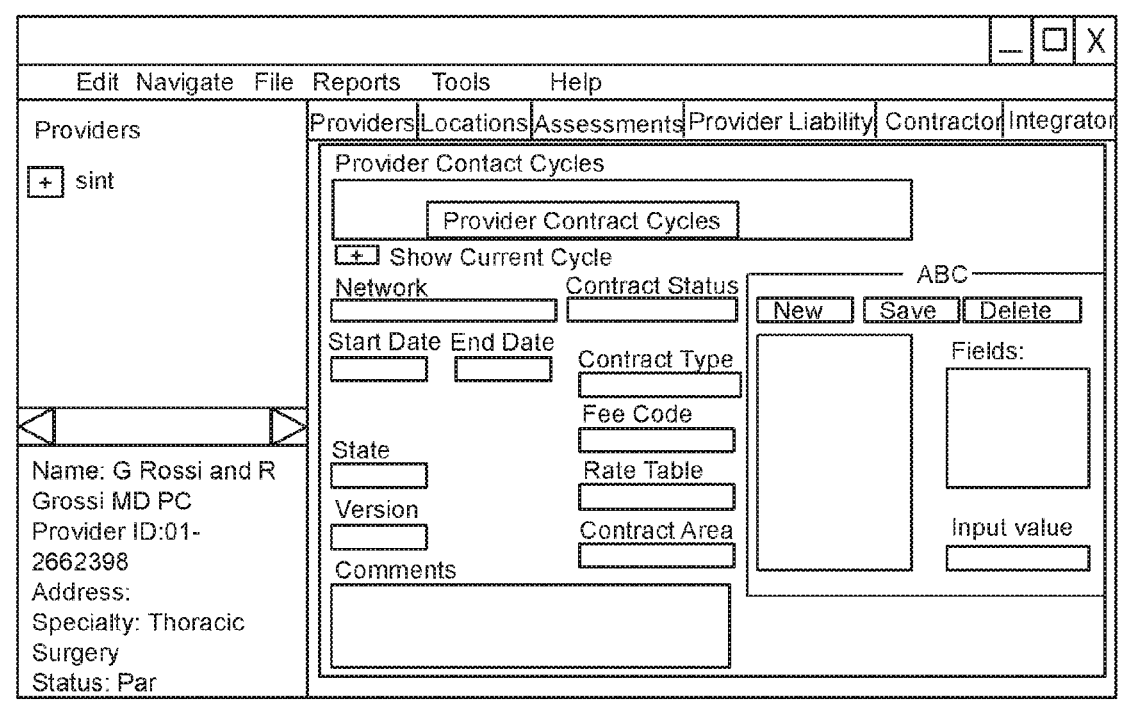

As may be seen in FIG. 7, a user may select Contracts from the Provider Mode, and may view information related to contract issues associated with a particular provider. Such information may include Provider Contract Cycles, Network, Start Date, End Date, Negotiator, State, Version, Contract Status, Contract Type, Fee Code, Rate Table, Contract Area, Termination Reason, Comments, and Provider Contract Attributes, which may be added to, deleted, or saved, for example.

Figure 8:
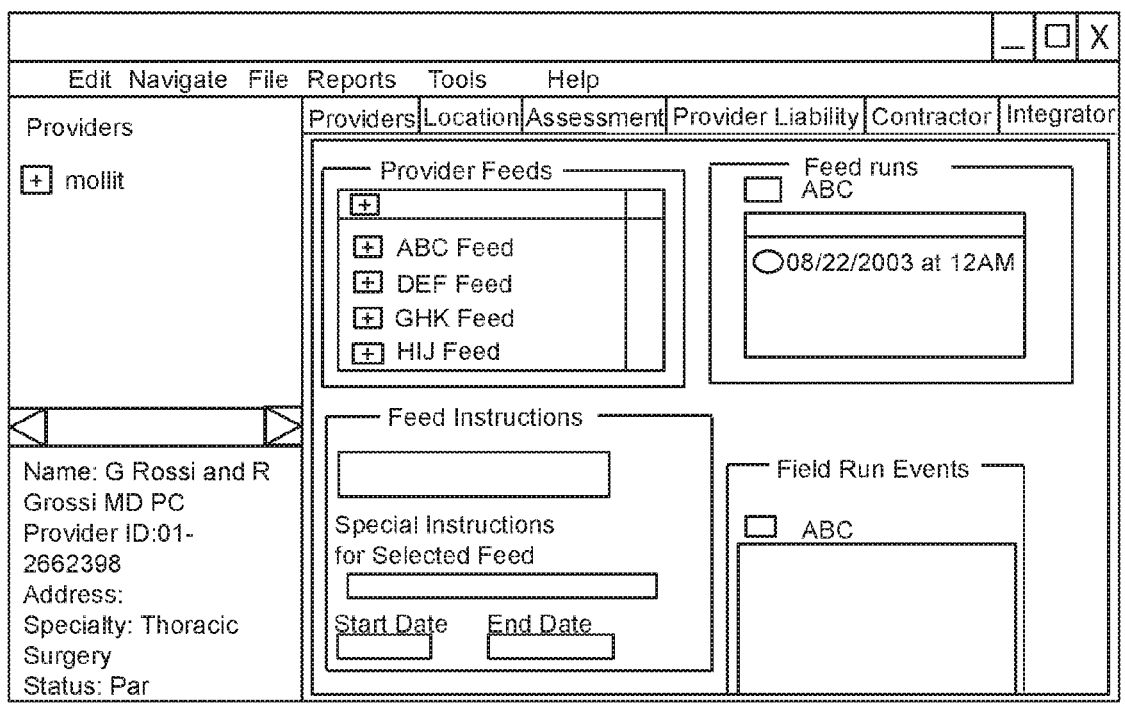

As may be seen in FIG. 8, a user may select Integrator from the Provider Mode, and may view information related to integrating issues associated with a particular provider. Such information may include Provider Feeds, Feed Instructions, Special Instructions for Selected Feed, Start Date, Stop Date, Feed Runs, and Feed Run Events, for example.

Under the Business Entity Mode, a user may search a business entity database for a business entity and select any such business entity identified to view information specific to that business entity. For example, when a user selects a particular business entity under the Business Entity Mode, the user may further select an application from a variety of applications, such as Business Entities, Locations, and Site Visits.

Figure 17:
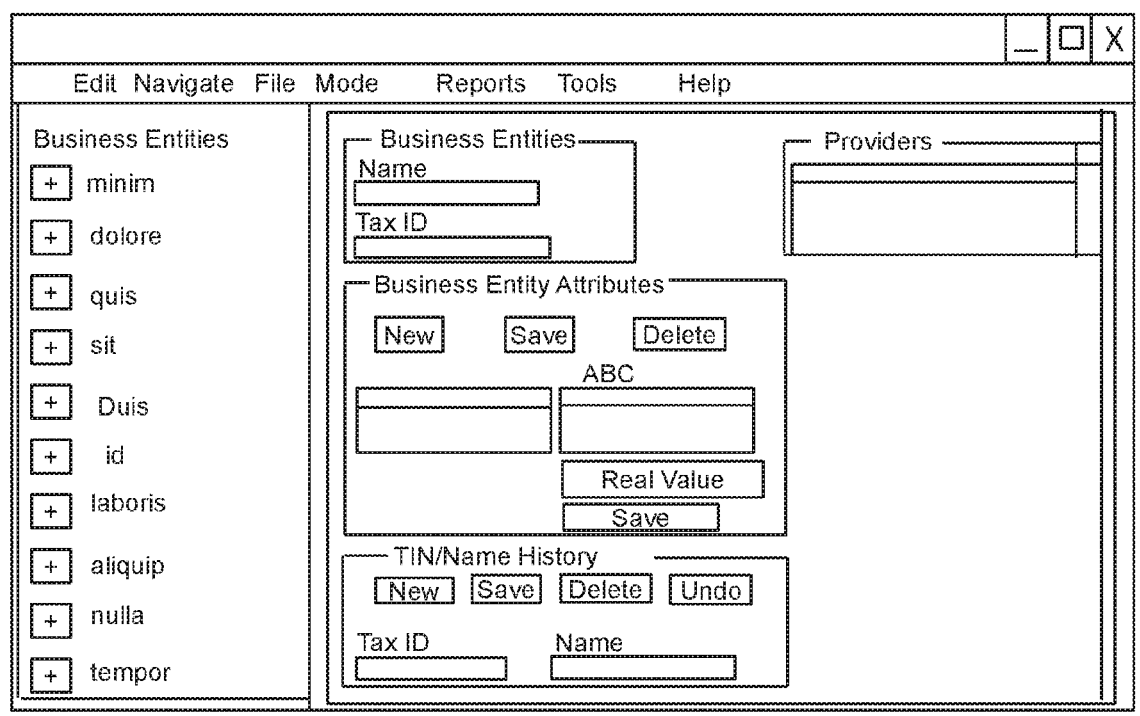

As may be seen In FIG. 17, a user may select Business Entities from the Business Entity Mode, and may view information related to a particular business entity. Such information may include Name, Tax ID, Providers, Business Entity Attributes, which may be added to, deleted, or saved, and TIN/Name History, which may also be added to, deleted, or saved, and further includes information regarding Tax ID and Name, for example.

Figure 39:
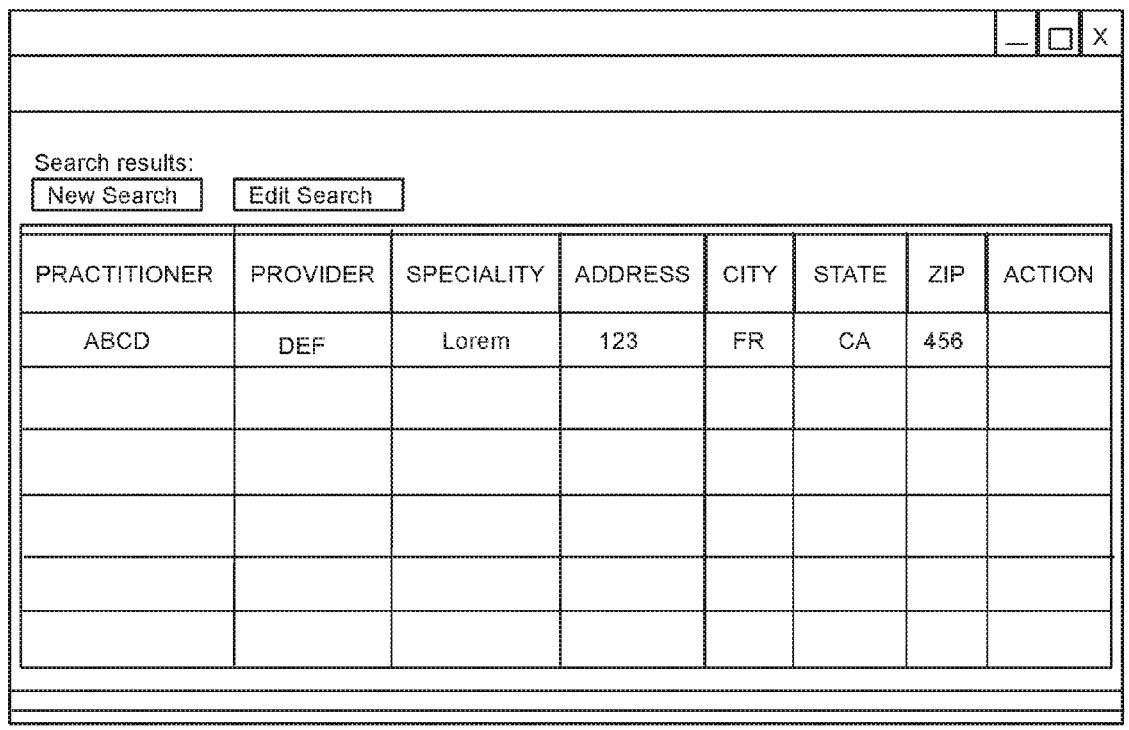

In another exemplary embodiment, the Internet portal may allow a user to perform tasks, such as an Enterprise Search or Initial Credentialing. For example, as seen in FIG. 37, the user may select Enterprise Search through the Internet portal, and further select searching parameters as desired by the user. Such parameters may be, for example, Search logic, In Network, Practitioner Search, Provider Search, Geographical Search, and ID Search. Any single or combination of parameters may be used according to the needs of the user. Results of such a search may be viewed in a listing format, as is shown in FIG. 39, or any other format known by those skilled in the art of displaying search results.

Figure 38:
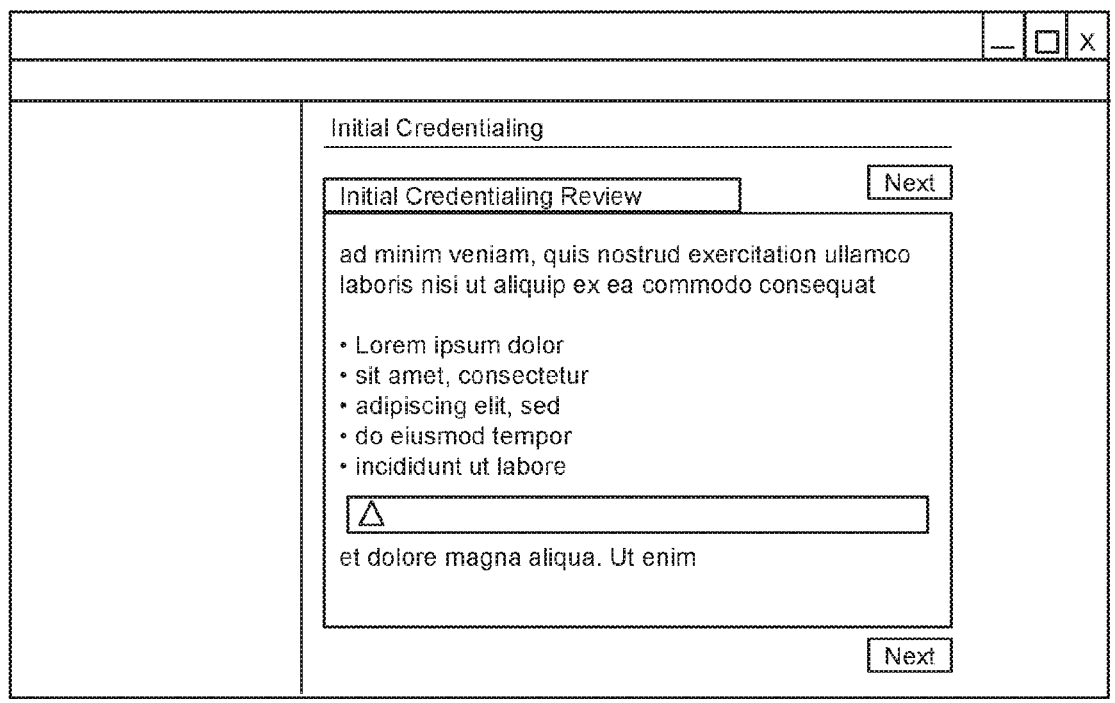

As may be seen in FIG. 38, a user may complete an initial credentialing application to help streamline the credentialing process which may be used by providers. For example, the user, who may be a practitioner, may select Initial Credentialing through the Internet portal, and complete the Initial Credentialing Review application as instructed. The information requested and the formatting used within the credentialing application may vary according to the needs of the receiving providers or other involved entities.

In yet another exemplary embodiment of the present disclosure, a user may access and edit reports through the Reporter in the Applications layer. For example, as is shown in FIG. 31, a user may reach a Reporter Main Menu by selecting the Reporter from the Applications layer. The Reporter Main Menu may provide a variety of functions selectable by the user, such as a Reporter Menu, a Report Template Configuration, and a Purge Expired Reports. As may be seen in FIG. 32, the user may further select Reporter Menu, from the Reporter Main Menu, to view a set of folders, each of which may contain a different type of report. The types of report folders maybe, for example, Administration Reports, Contracting Reports, Credentialing Reports, Maintenance Reports, Management Reports, Provider Relations Reports, Site visit Reports, and System Reports. If, for example, the user desires to access credentialing reports, the user may further select Credentialing Reports from the Reporting Menu. As is shown in FIG. 33, the selection of Credentialing Reports by the user may provide the user with a selection of Templates from which to choose from, and list of reports, which may be further accessed and edited, and which may be further identified by Report (or template type), Owner, Date Created, and Dated Expires. An Action, which may be identified by icon, may also be provided for each listed report and may allow the user to more quickly perform a particular task.

Figure 28:
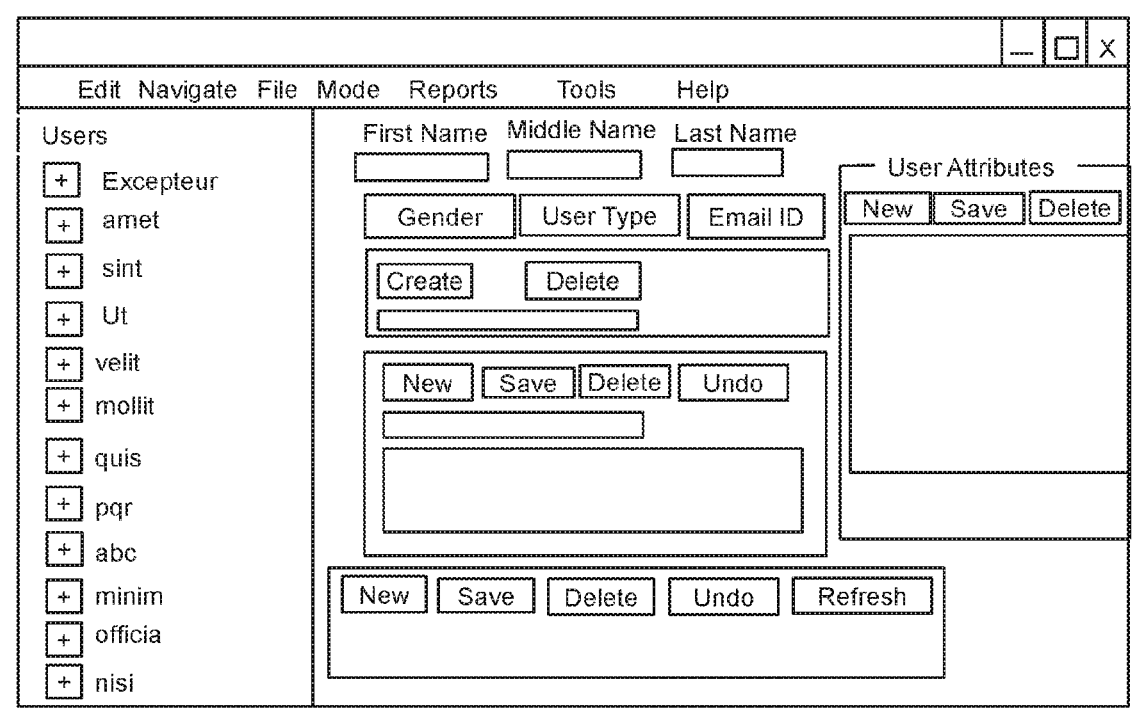
Figure 29:
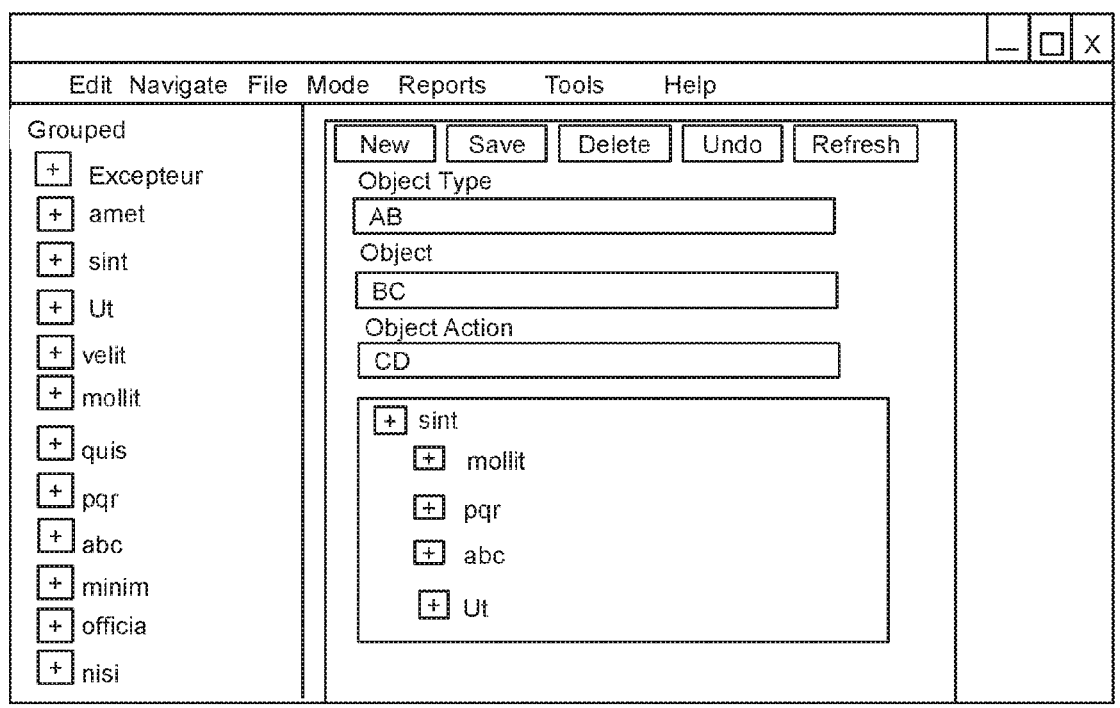
Figure 30:
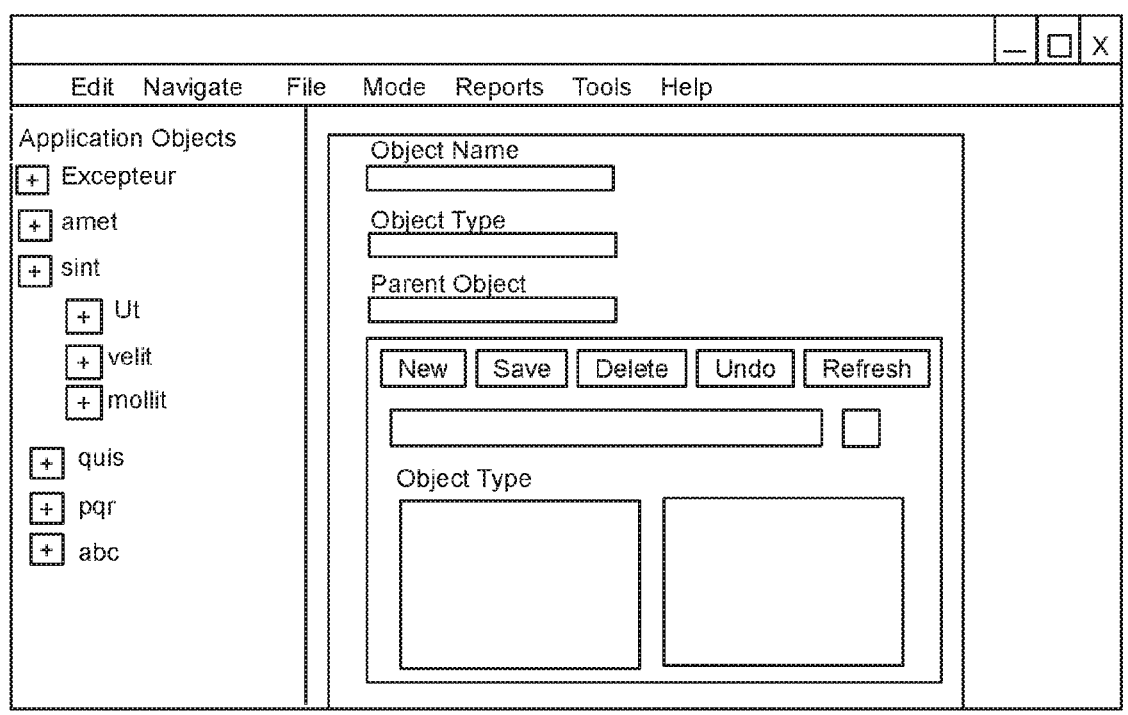

In another exemplary embodiment of the present disclosure, users may have various levels of access throughout the system applications, and for purposes of security, a particular user's accessibility, group, or application object may be viewed and/or edited. For example, as is shown in FIG. 28, a user may, through the Security Manager, view a list of users, and for each user, view information associated with a particular user. Such information may be further defined and further selectable under headings, such as Users, Groups, Application Objects, and Folder Editor, for example. Under Users, information on a particular user may be seen, such as First, Middle, and Last Name, Gender, User Type, Email Address, User Attributes, which may be added to, deleted, or saved, User Database Account, which may be further Edited, Created, or Deleted, User Account Status, DB Username, Group, which may be added to, deleted, or saved, Groups for User, and Territory. AS is shown in FIG. 29, user information under the Groups heading may be Permissions, which may further be added to, deleted, or saved, Object Type, Object, Object Action, and Allow, for example. In FIG. 30, information under the Application Objects heading may be, for example, Full Object Description, Object Name, Object Type, Parent Object, Object/Database Object Relationships, and DB Object.

Figure 34:
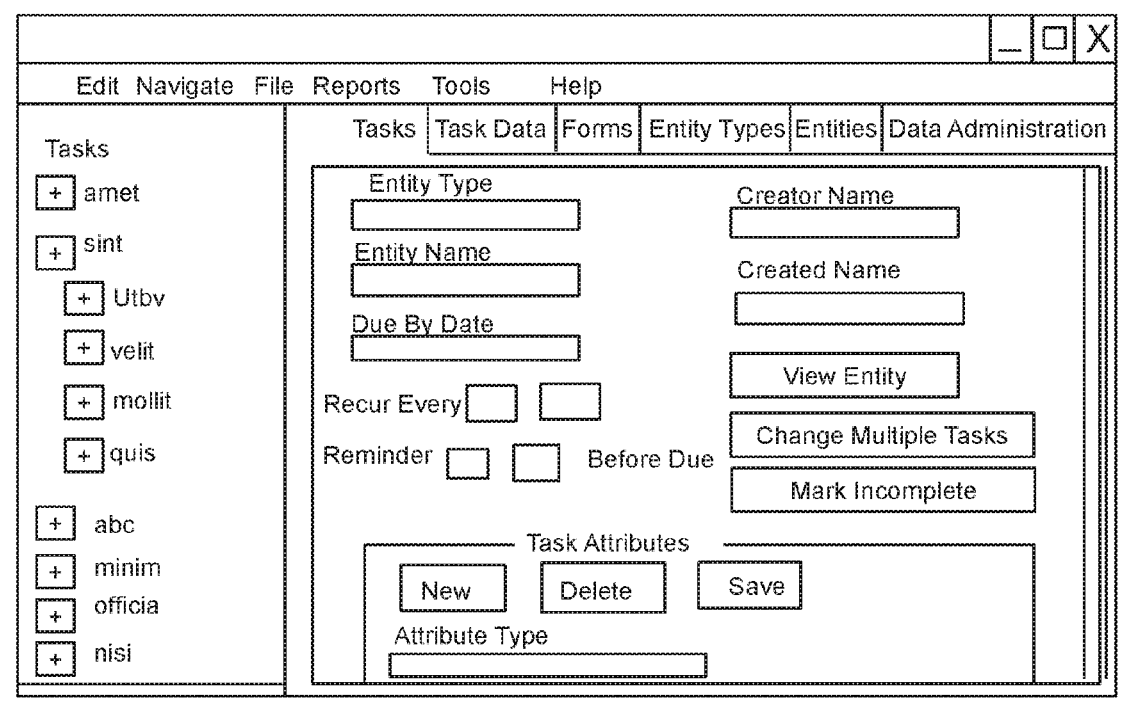
Figure 35:
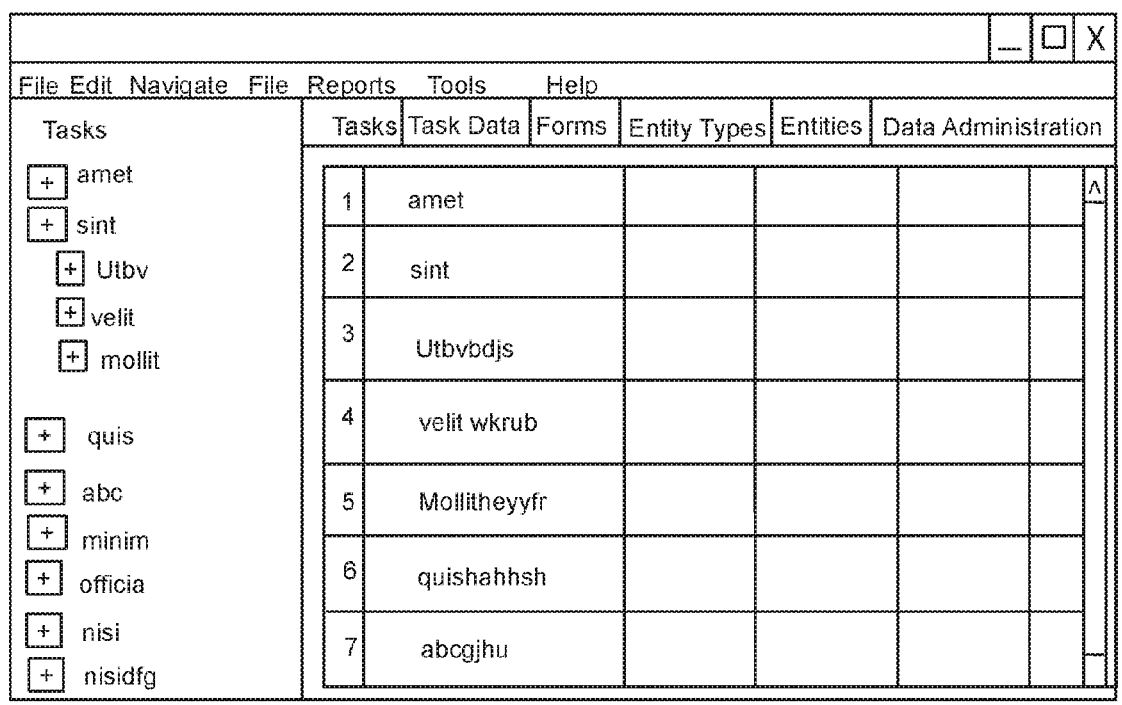
Figure 36:
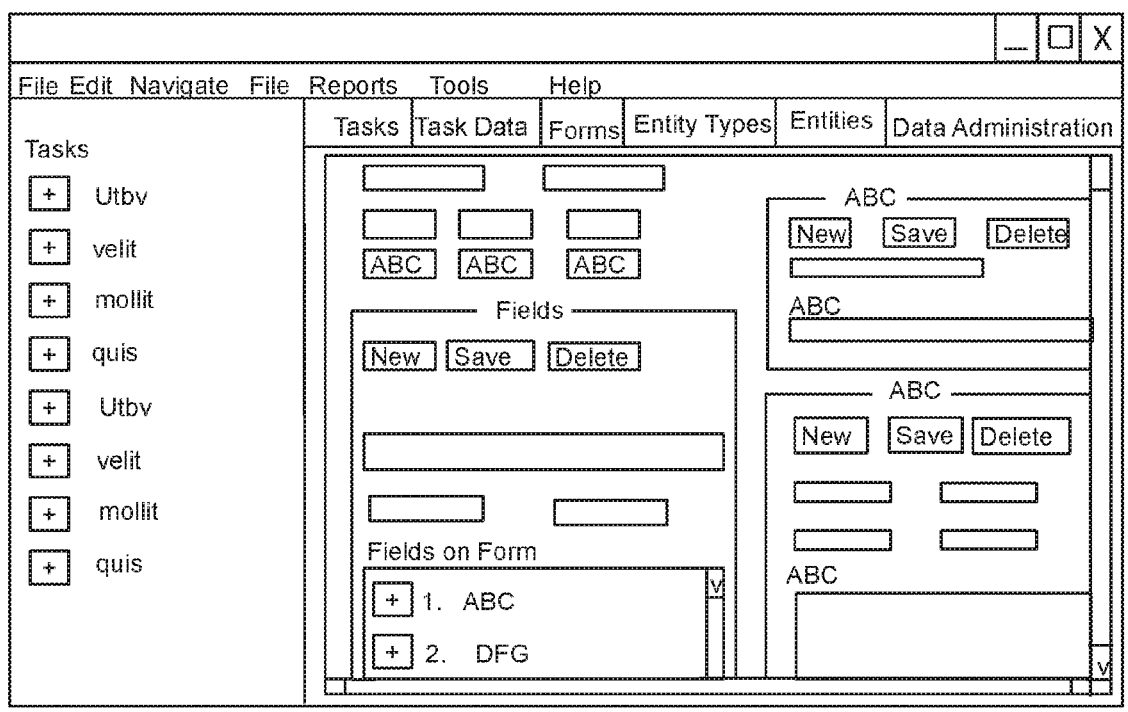

In another exemplary embodiment of the present disclosure, a user may wish to review and/or edit various tasks associated with a particular user, entity, group, practitioner, provider, or the like, and is illustrated in FIGS. 34-36. For example, as may be seen in FIG. 34, the user may select site visits and further select a task or a set of tasks associated with a particular user—by selecting that user from a list of users. Upon selection of the task or set of tasks, the user may view information related to that task, such as Tasks, Tasks Data, Forms, Entity Types, Entities, and Data Administration, for example. As may also be seen in FIG. 34, information organized under Tasks may be, for example, Entity Type, Entity Name, Form Name, User Name, Status, Priority, Due By Date, Recur every, Reminder before due, Creator Name, Created Name, Sync Date, Start Date, Completed Date, Analysis Date, Task Attributes, which may be added to, deleted or saved, Attribute Type, Attribute Value, and Attributes. The user may also take additional actions, such as View Entity, Change Multiple Tasks, Mark incomplete and Edit Task, for example, by selecting an icon named for each such action, respectively. As is shown in FIG. 35, the user may also select information organized under Task Data, which may be, for example, Number, Description, Value, Initial Value, Notes, User, and Stamped, for example. In FIG. 36, taskinformation organized under Forms may be, for example, Form Name, Version, Unique Identifier, Allow PDA Create, Form Type, Fields, which may be added to, deleted or saved, Field Type, Required, Unique Identifier, Tag Group, Sequence, Hidden/Visible, Allow Override, Fields on Form, Field Values, which may be added to, deleted or saved, Rules, which may be added to, deleted or saved, Rule Type, Comparison Type, Operator, Compare Value, and Field Rules. The user may also take further actions, such as Form Wizard, Copy Form and New Form Version, for example, by selecting the icon for each sort of action, respectively.

Figure 20:
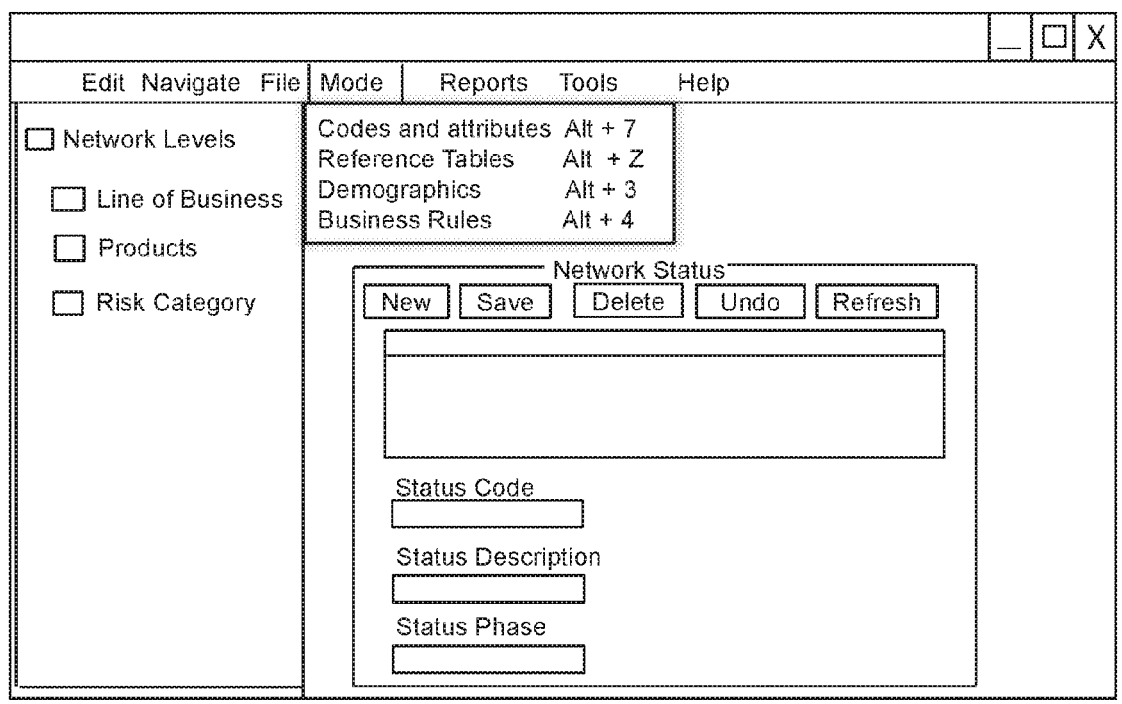

In yet another exemplary embodiment of the present disclosure, a user may wish to review, edit or manipulate data within the system. For example, a user may, via the applications layer, access a Data Administrator to review and edit data within a variety of modes. As can be seen In FIG. 20, such modes may include, for example, Codes and Attributes, Reference Tables, Demographics, and Business Rules. When a user selects the Reference Tables Mode from the Data Administrator, the user may view information relating to Network Levels, Networks, Specialties, Institutions, for example.

As may also be seen in FIG. 20, Information relating to Network Levels may be expressed in terms of, for example, Line of Business, Products, or Risk Category. Further, this information may include areas such as, for example, Description, Long Description, Parent Network, Network Status, which may be added to, deleted or saved, Status Code, Status Description, and Status Phase.

Figure 21:
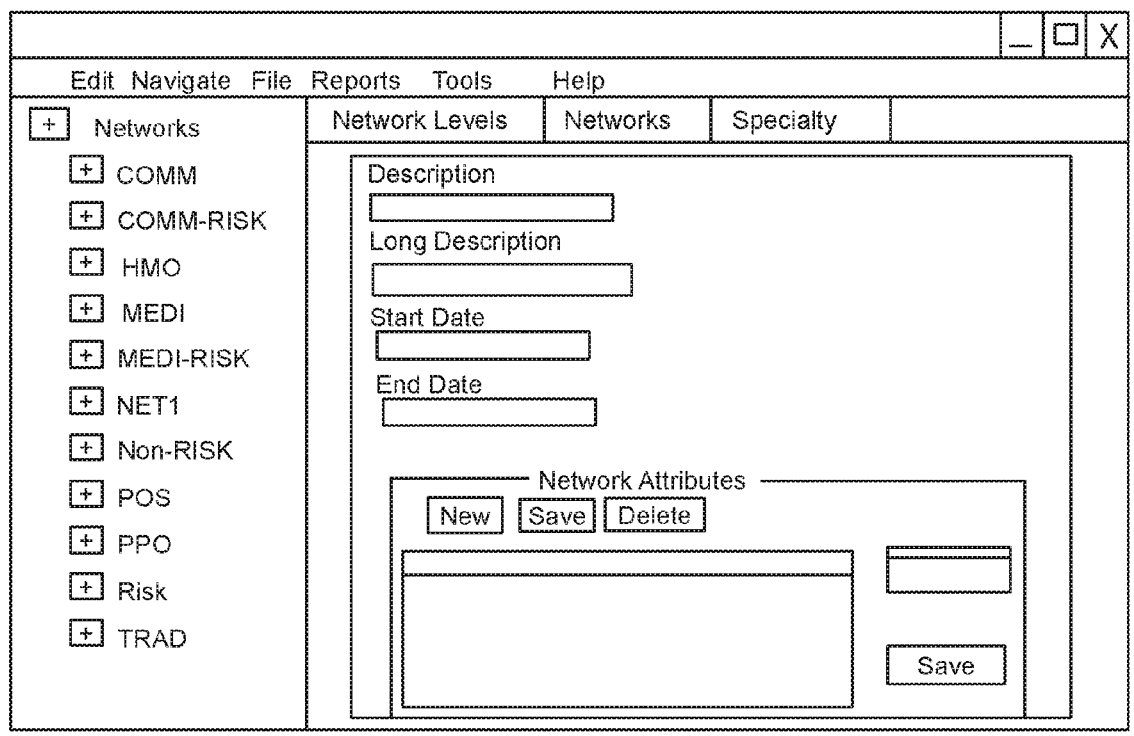

As may be seen in FIG. 21, Information relating to Networks may be expressed by, for example, the type of network, such as COMM, COMM-RISK, HMO, MEDI, MEDI-RISK, NET1, Non-RISK, POS, PPO, Risk, and TRAD. Further, this information may include areas such as, for example, Description, Long Description, Start Date, End Date, Network Level, Parent Network, and Network Attributes, which may be added to, deleted or saved.

Figure 22:
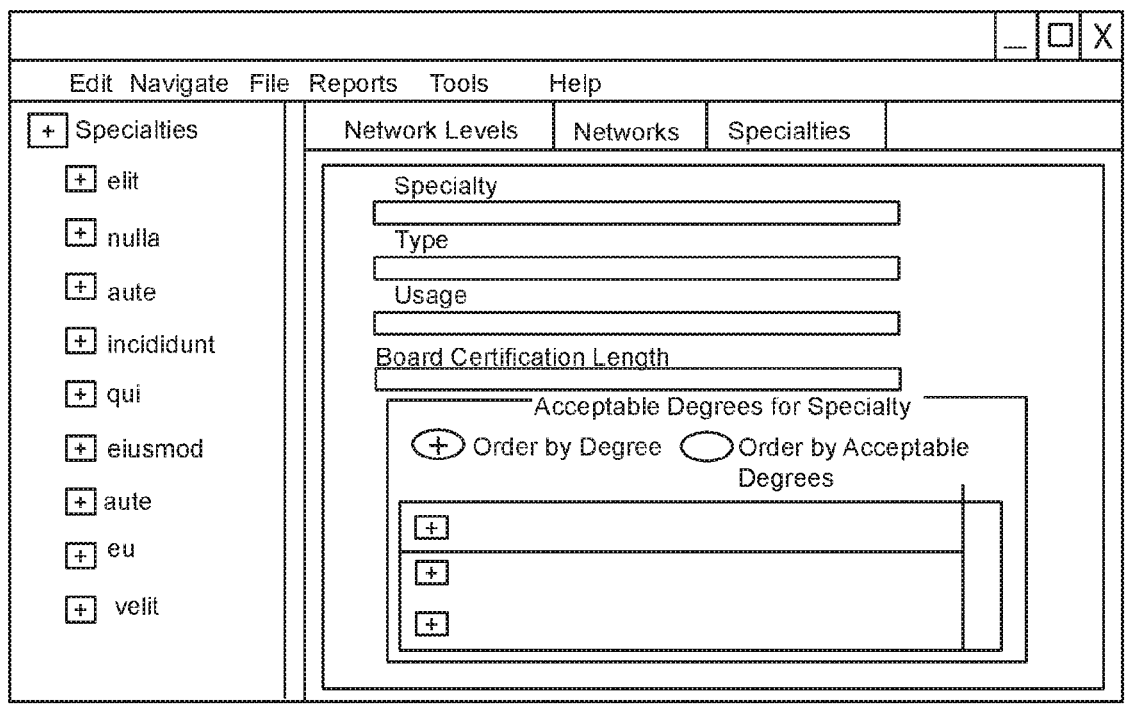

As may be seen in FIG. 22, Information relating to Specialties may be expressed by, for example, any sort of specialty associated to the practice of medicine or the medical industry, including practitioners, entities, facilities, equipment type, area of practice, and the like. Further, this information may include areas such as, for example, Specialty, Type, Usage, Board Certification Length, Ancillary, site Visit Required, and Acceptable Degrees for Specialty, which may be ordered by Degree or by Acceptable Degrees.

Figure 23:
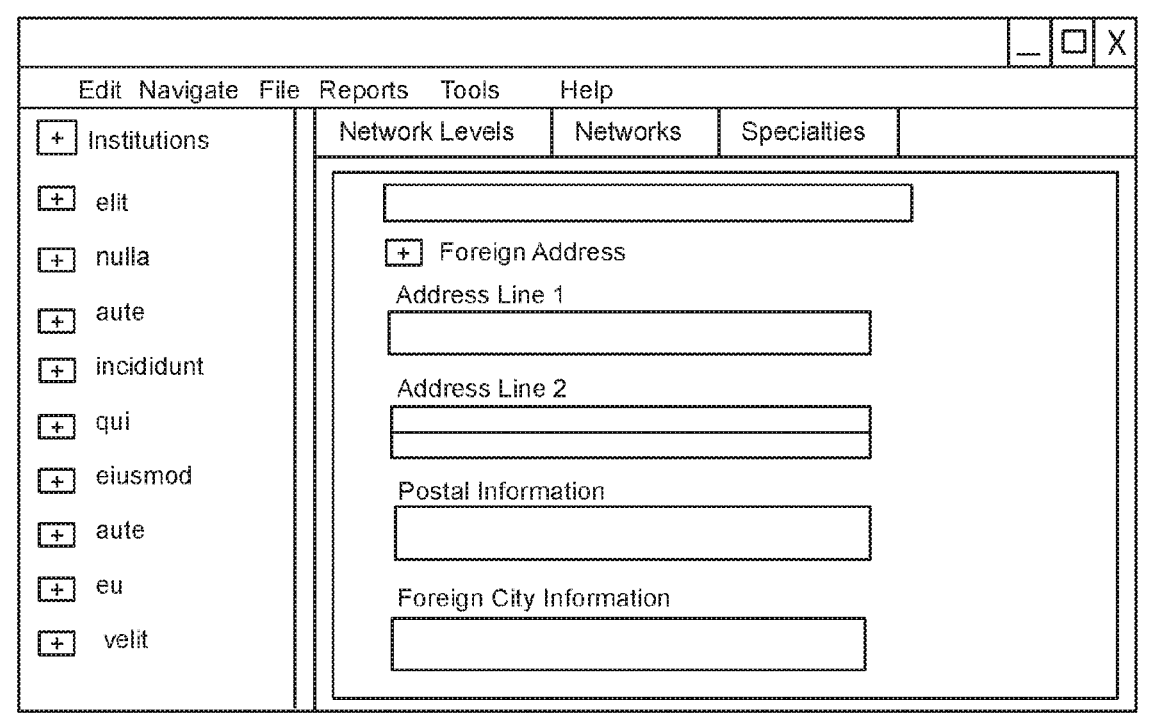

As may be seen in FIG. 23, Information relating to Institutions may be expressed by, for example, any institution or facility, be it public or private, for-profit or non-profit, foreign or domestic, educational, religious, and the like, as found within the database. Further, this information may include, for example, all features relating to a physical address, as well as information relating to an associated foreign city.

Figure 24:
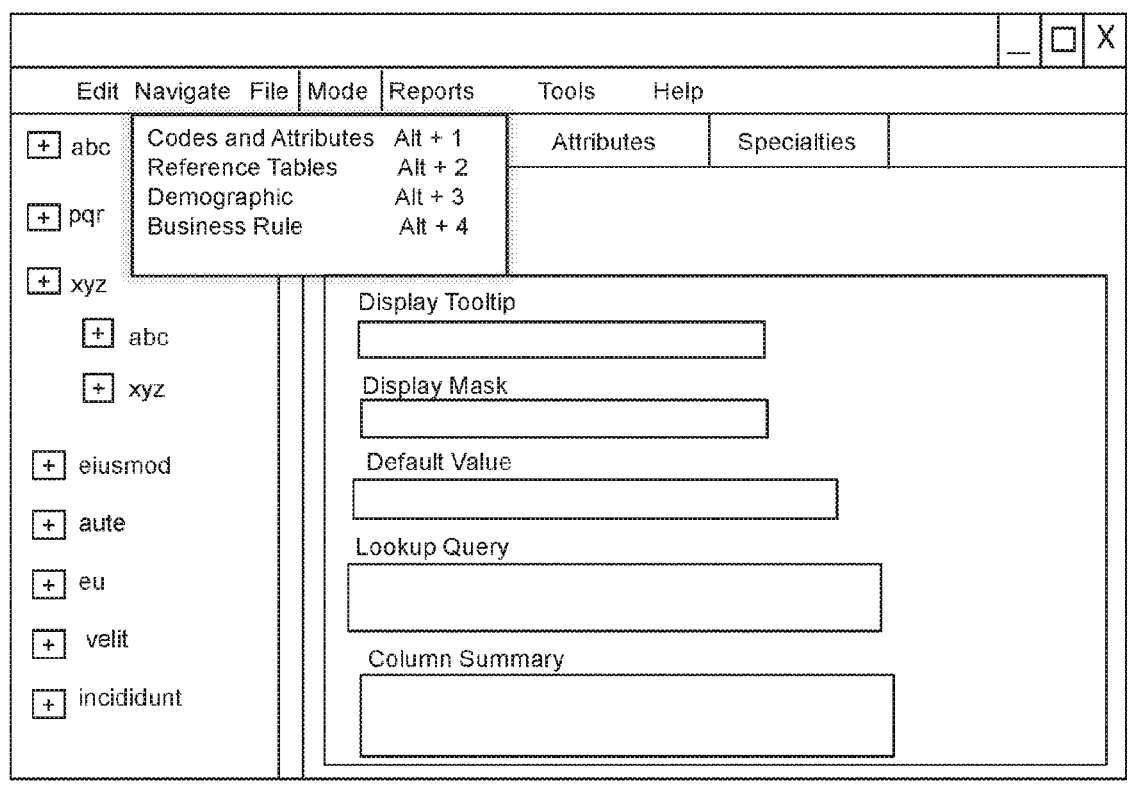

As shown in FIG. 24, the user may review and/or edit information relating to, for example, Codes, Attributes, and Data Dictionary under the Codes and Attributes Mode of the Data Administrator. For example, information relating to Data Dictionary may be Display Label, Display Tolltip, Display Mask, Default Value, Field Required, Type, Lookup Query, and Column Summary, for example.

Figure 25:
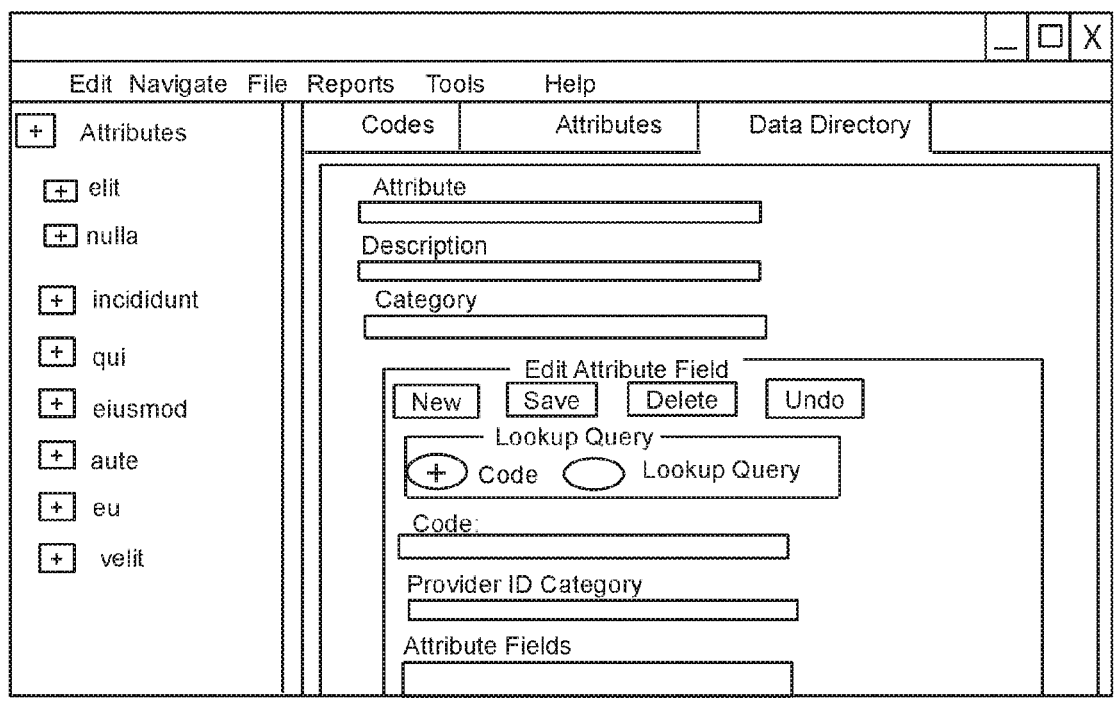

As may be seen in FIG. 25, information relating to Attributes may be expressed by various categories such as, for example, Business Entity, Credentialed Items, Location, Network, Practitioner Contract, Practitioner Credentialing Cycle, Practitioner, Provider Affiliation, Provider Assessment Cycle, Provider Contract, Provider Location, Provider Network Cycle, Provider, User and Virtual Provider ID. Further, this information may include, for example, Attribute, Description, Category, Allow Search, Order By/Edit Attribute Fields, which may be added to, deleted or saved, Field Name, Data Type, Lookup Query, Code, Provider ID Category, Order By, and Attribute Fields.

Figure 26:
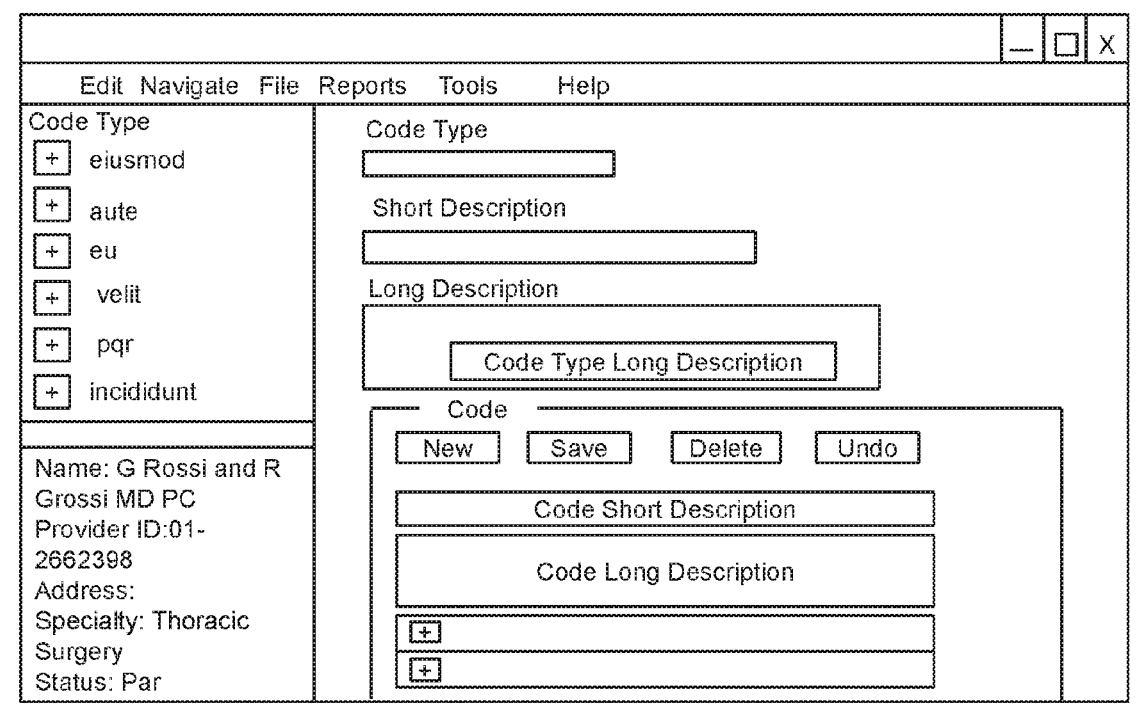

As may be seen in FIG. 26, information relating to Codes may be expressed by any sort of Code Type as found in any database accessible by the system. Further, this information may include, for example, Code Type, Short Description, Long Description, Codes, which may be added to/deleted or saved, Code Short Description, and Code Long Description.

Figure 27:
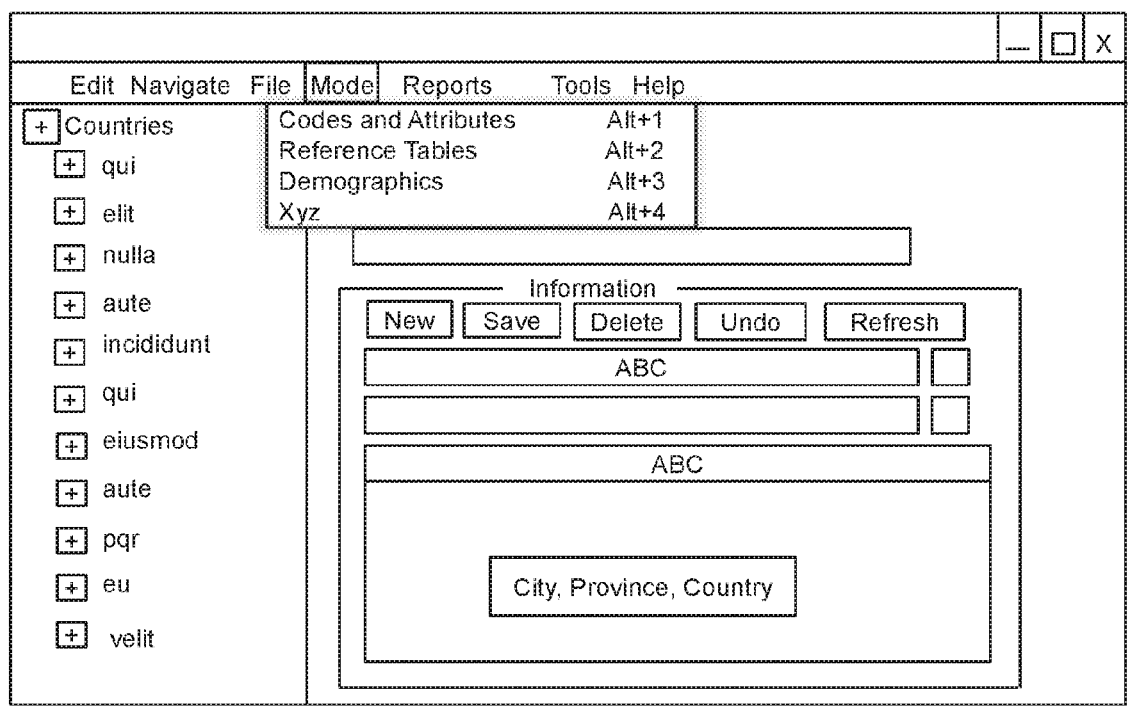

As may be seen in FIG. 27, the user may review and/or edit information relating to the Demographics Mode of the Data Administrator. For example, the user may select Demographics from the Mode section of the Data Administrator, and further a category of information, such as, for example, Cities, Counties/Provinces, US Postal Codes, Countries, and Territories.

As may also be seen in FIG. 27, information relating to Countries may be accessed by the user by selecting a country from a list of countries found with the databases accessible by the system. Further, this information may include, for example, Country Name and City or Province, which may be added to, deleted, and saved.

It is to be understood that the figures and descriptions of the present disclosure have been simplified to illustrate elements that are relevant for a clear understanding of the present disclosure, while eliminating, for the purpose of clarity, many other elements found in typical enterprise management systems and methods of using the same. Those of ordinary skill in the art may recognize that other elements and/or steps are desirable and/or required in implementing the present disclosure. However, because such elements and steps are well known in the art, and because they do not facilitate a better understanding of the present disclosure, a discussion of such elements and steps is not provided herein. The disclosure herein is directed to all such variations and modifications to such elements and methods known to those skilled in the art.

Moreover, those of ordinary skill in the art may recognize that many modifications and variations of the present disclosure may be implemented without departing from the spirit or scope of the disclosure. Thus, it is intended that the present disclosure covers the modifications and variations of this disclosure provided they come within the scope of the appended claims and their equivalents.

We claim:

1. A method for providing a health care enterprise management system comprising a routing layer, an application layer, a business rules layer, a data language normalization engine, and a core database layer, the method comprising:
    maintaining a rules engine in the business rules layer, the rules engine comprising a plurality of selectable rules, wherein each of the plurality of selectable rules has rule attributes that define each of the selectable rules;
    maintaining health care related data in a core database of the core database layer, for applying to different applications;
    associating data with the health care related data in the core database by a link from a data entry point in the core layer to an external data node of said entry point to the world-wide web or an Intranet;
    maintaining a dedicated database resident in the business rules layer, the dedicated database having stored therein a plurality of health care business rules comprising at least one rule having multiple layers such that satisfaction of one of the rule attributes of at least one layer will trigger application of other attributes of the at least one layer;
    maintaining a history of rules and rules changes in both said core database resident in the core layer and said dedicated database resident in said business rules layer, the dedicated database having rule tracking and rule reporting;
    providing, with the routing layer, connectivity between said application layer, said business rules layer, and said core database so that said health care related data is simultaneously accessible by said application layer, said business rules layer, and said core database; and
    providing, by the business rules layer, a communicative interface between each of a plurality of graphical user interfaces of the application layer, a plurality of health care business rules, and said health care related data.

2. The method of claim 1, wherein providing connectivity comprises providing connectivity with the routing layer between said application layer, said business rules layer, said core database and an external application.

3. The method of claim 1, wherein said plurality of health care business rules comprise at least one subset of rules that is correspondent to each of said plurality of graphical user interfaces.

4. The method of claim 1, wherein said plurality of health care business rules include a defined set of allowable interactions between each of said plurality of graphical user interfaces and said core database.

5. The method of claim 1, wherein said plurality of health care business rules comprise credentialing rules that allow for credentialing of health care providers that have information within said health care related data.

6. The method of claim 1, wherein said health care related data comprises any of health care provider information, patient information, insurer information, plan information, institution information, entity information, or transaction information.

7. The method of claim 1, wherein said plurality of applications comprises a queue that causes, responsively to one or more user instructions, one or more rules in said business rules layer to be applied to force the performance of tasks in a predetermined order.

8. The method of claim 1, further comprising allowing for modifications by the rules engine to the rules from one or more applications in the application layer.

9. The method of claim 1, wherein said at least one rule having multiple layers includes successive layers wherein a subsequent layer is applied as each successive layer of the multiple layers of the at least one rule is satisfied, wherein each layer of the multiple layers has a series of attributes, and satisfaction of all attributes of the at least one layer will trigger application of the subsequent layer.

10. The method of claim 1, wherein the plurality of health care business rules are subject to change and the changes to the rules are enforced on all data in both databases upon execution of a new rule.

11. A computer program product for controlling a health care enterprise management system comprising a routing layer, an application layer, a business rules layer, a data language normalization engine, and a core database layer, the computer program product comprising at least one non-transitory computer-readable medium having computer-readable program instructions stored therein, the computer-readable program instructions comprising instructions, which when performed by an apparatus, are configured to cause the apparatus to at least:
    maintain a rules engine in the business rules layer, the rules engine comprising a plurality of selectable rules, wherein each of the plurality of selectable rules has rule attributes that define each of the selectable rules;
    maintain health care related data in a core database of the core database layer, for applying to different applications;
    associate data with the health care related data in the core database by a link from a data entry point in the core layer to an external data node of said entry point to the world-wide web or an Intranet;
    maintain a dedicated database resident in the business rules layer, the dedicated database having stored therein a plurality of health care business rules comprising at least one rule having multiple layers such that satisfaction of one of the rule attributes of at least one layer will trigger application of other attributes of the at least one layer;
    maintain a history of rules and rules changes in both said core database resident in the core layer and said dedicated database resident in said business rules layer, the dedicated database having rule tracking and rule reporting;
    provide, with the routing layer, connectivity between said application layer, said business rules layer, and said core database so that said health care related data is simultaneously accessible by said application layer, said business rules layer, and said core database; and
    provide, by the business rules layer, a communicative interface between each of a plurality of graphical user interfaces of the application layer, a plurality of health care business rules, and said health care related data.

12. The computer program product of claim 11, wherein providing connectivity comprises providing connectivity with the routing layer between said application layer, said business rules layer, said core database and an external application.

13. The computer program product of claim 11, wherein said plurality of health care business rules comprise at least one subset of rules that is correspondent to each of said plurality of graphical user interfaces.

14. The computer program product of claim 11, wherein said plurality of health care business rules include a defined set of allowable interactions between each of said plurality of graphical user interfaces and said core database.

15. The computer program product of claim 11, wherein said plurality of health care business rules comprise credentialing rules that allow for credentialing of health care providers that have information within said health care related data.

16. The computer program product of claim 11, wherein said health care related data comprises any of health care provider information, patient information, insurer information, plan information, institution information, entity information, or transaction information.

17. The computer program product of claim 11, wherein said plurality of applications comprises a queue that causes, responsively to one or more user instructions, one or more rules in said business rules layer to be applied to force the performance of tasks in a predetermined order.

18. The computer program product of claim 11, wherein the computer-readable program instructions further comprise instructions, which when performed by an apparatus, are configured to cause the apparatus to at least allow for modifications by the rules engine to the rules from one or more applications in the application layer.

19. The computer program product of claim 11, wherein said at least one rule having multiple layers includes successive layers wherein a subsequent layer is applied as each successive layer of the multiple layers of the at least one rule is satisfied, wherein each layer of the multiple layers has a series of attributes, and satisfaction of all attributes of the at least one layer will trigger application of the subsequent layer.

20. The computer program product of claim 11, wherein the plurality of health care business rules are subject to change and the changes to the rules are enforced on all data in both databases upon execution of a new rule.

* * * * *